United States Patent [19]
Bui

[11] Patent Number: 5,324,323
[45] Date of Patent: Jun. 28, 1994

[54] MULTIPLE CHANNEL CARDIOSYNCHRONOUS MYOPLASTY APPARATUS

[75] Inventor: Tuan S. Bui, Englewood, Colo.

[73] Assignee: Telectronics Pacing Systems, Inc., Englewood, Colo.

[21] Appl. No.: 942,669

[22] Filed: Sep. 9, 1992

[51] Int. Cl.[5] .......................................... A61N 1/362
[52] U.S. Cl. ...................... 607/119; 607/132; 600/16
[58] Field of Search ........ 128/419 PG, 419 P, 419 R, 128/421, 422, 783, 784, 785, 786; 623/3; 600/16-18; 607/9, 132, 72, 116, 119

[56] References Cited

U.S. PATENT DOCUMENTS

| | | |
|---|---|---|
| 4,666,443 | 5/1987 | Portner ................................ 623/3 |
| 4,735,205 | 4/1988 | Chachques et al. . | 
| 4,791,911 | 12/1988 | Magovern ........................ 600/36 |
| 4,813,952 | 3/1989 | Khalafalla ........................ 623/3 |
| 4,919,661 | 4/1990 | Gibney ............................ 623/3 |
| 4,979,936 | 12/1990 | Stephenson et al. ............ 600/16 |
| 5,009,229 | 4/1991 | Grandjean et al. . | 
| 5,067,960 | 11/1991 | Grandjean ...................... 623/3 |
| 5,069,680 | 12/1991 | Grandjean ...................... 623/3 |
| 5,089,019 | 2/1992 | Grandjean ...................... 623/3 |
| 5,098,442 | 3/1992 | Grandjean ...................... 623/3 |
| 5,158,097 | 10/1992 | Christlieb ........................ 600/16 |
| 5,195,518 | 3/1993 | Mannion et al. ................ 600/16 |
| 5,205,810 | 4/1993 | Guiraudon et al. ............. 600/16 |

OTHER PUBLICATIONS

Magovern, G. J. et al., "The Allergheny Hospital Experience", *Cardiomyoplasty*, pp. 159-170, eds. Carpentier, A. et al., Futura Publishing Inc., Mt. Kisco, N.Y., 1991.

*Primary Examiner*—Lee S. Cohen
*Assistant Examiner*—Jeffrey R. Jastrzab
*Attorney, Agent, or Firm*—Gottlieb, Rackman & Reisman

[57] ABSTRACT

A neuromuscular stimulation apparatus and procedure, which employs multiple channels of stimulation for the purpose of supplying directional control of blood flow in addition to augmenting the force of contraction. The apparatus comprises multiple channel stimulation electrodes and a multiple channel cardiosynchronous stimulator to selectively stimulate various sections of the skeletal muscle. The amplitudes of the stimulation pulses and the time delay following a cardiac event may be selected for each channel to appropriately stimulate the muscle to control the order of contraction of particular muscle fibers and thereby to govern the direction of blood flow.

20 Claims, 17 Drawing Sheets

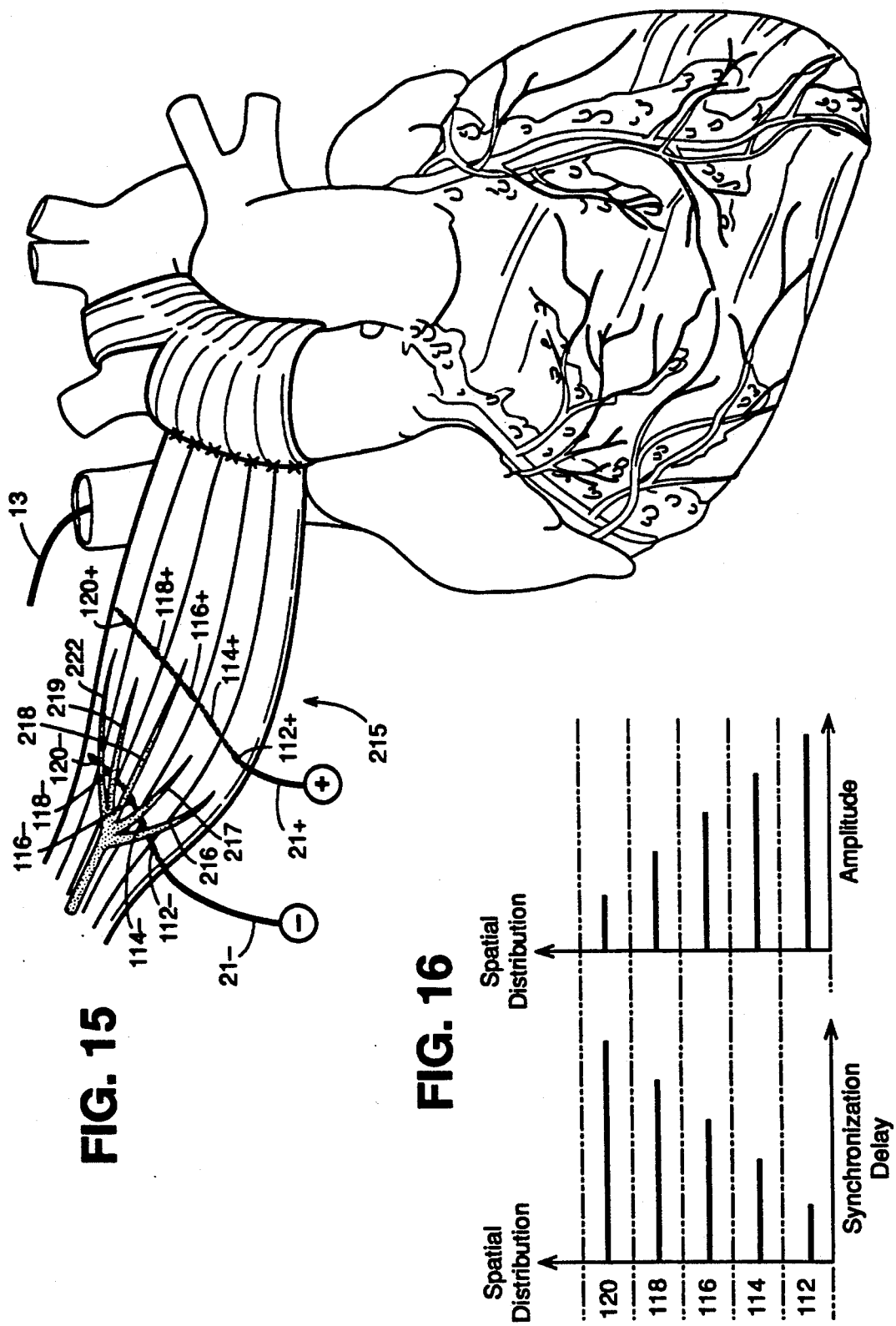

MULTIPLE CHANNEL CARDIOSYNCHRONOUS MYOPLASTY APPARATUS

TECHNICAL FIELD

The present invention relates to implantable medical bioelectrical stimulating devices for performing skeletal muscle assistance of the heart, including procedures such as cardiomyoplasty, aortomyoplasty or skeletal muscle ventricles, and more particularly to a multiple channel bioelectrical stimulating device employing a multi-electrode lead.

BACKGROUND OF THE INVENTION

Severe chronic cardiac insufficiency arising from cardiac disease or injury shortens and degrades the quality of life of many patients. One form of severe chronic cardiac insufficiency, congestive heart failure, is a pathophysiological state in which cardiac output is inadequate to meet physiological requirements of the body. The mortality rate for congestive heart failure is greater than 50% within 5 years of onset. Treatments for severe chronic cardiac insufficiency include heart transplants, artificial heart implants and cardiomyoplasty. Cardiac transplantation, using cyclosporine to inhibit tissue rejection, is a very successful technique for prolonging a cardiac patient's life, improving the survival rate to 80% at 1 year. However, the transplant operation is very expensive and heart availability is limited. The artificial heart has had very limited success.

Dynamic cardiomyoplasty is a surgical and electrical therapeutic technique in which a skeletal muscle flap is dissected from a patient, while maintaining its innervating neural tissues and neurovascular structures, and surgically placed around the patient's heart. A bioelectrical stimulation device with an electrical pulse generator and intramuscular electrodes are implanted which perform muscle electrical stimulation in synchrony with ventricular systole to support cardiac pumping. In functional electrical stimulation (FES) applications, one or more intramuscular electrodes are placed within a muscle body. Because intramuscular electrodes are firmly positioned with respect to nerve branches, they are advantageous for promoting long-term functional stability, giving rise to repeatable contractions.

A protocol of sequential and progressive skeletal muscle electrical stimulation causes glycolytic muscle fibers, predominant in skeletal muscle, to take the form of oxidative fibers. Oxidative fibers are resistant to fatigue and have histochemical and biochemical characteristics of myocardium. Stimulated skeletal muscle transforms into a fatigue-resistant state suitable for chronic ventricular assistance, enabling dynamic cardiomyoplasty. The skeletal muscle is then trained to function in the manner of cardiac muscle to assist the heart in increasing the patient's cardiac output. This permits skeletal muscle assistance of a patient's ailing heart muscle.

G. J. Magovern, in U.S. Pat. No. 4,791,911, entitled "Method of Cardiac Reconstructive Surgery", issued Dec. 20, 1988, discloses a surgical method of reconstructing damaged cardiac muscle using a latissimus dorsi skeletal muscle autograft.

J. C. Chachques et al., in U.S. Pat. No. 4,735,205, entitled "Method and Apparatus including a Sliding Insulation Lead for Cardiac Assistance", issued Apr. 5, 1988, discloses a suitable electrode configuration used in a system which provides muscle stimulation for a muscle surgically adapted to perform myocardial substitution. The leads have variable electrode surface areas which are adjusted at the time of surgical implantation to expose a desired length of electrode surface area extending through the muscle. At implantation, a tubular insulation sheath which overlies a conductor within the lead may be extended over or retracted from the conductor to expose a desired length of conductor. The exposed conductor acts as a muscle stimulation electrode.

P. A. Grandjean et al., in U.S. Pat. No. 5,009,229, entitled "Steroid Eluting Intramuscular Lead", issued Apr. 23, 1991, describes an intramuscular lead which is adapted from a type of cardiac pacing lead. This lead includes an insulated wire body, an electrode, a strand of suture material extending the entire length of the lead and distal to the electrode, and a curved needle attached to the distal end of the strand of suture material. The suture material is treated with a steroid drug, such as glucocorticosteroid, which, upon chronic implantation, is eluted from the suture material to treat tissue inflammation or damage caused by the implantation procedure or subsequent irritation. Although this lead may avoid or lessen damage to nerves caused by electrical stimulation, it does not diminish the high current flows which are required to stimulate muscle contraction.

In the aforementioned devices and methods, skeletal muscles have been employed to augment cardiac performance in patients with dilated or ischemic cardiomyopathy. In the procedure of cardiomyoplasty, the patient's latissimus dorsi muscle is wrapped around the heart and stimulated to contract during systole, in synchronization with the heart. In aortomyoplasty, the latissimus dorsi muscle is wrapped around the aorta and stimulated to contract during cardiac diastole. The latter technique is termed counterpulsation. Other manifestations of counterpulsation include a skeletal muscle ventricle technique in which the latissimus dorsi muscle is wrapped around a small diameter cylinder or cone. The muscle pump is then connected into the circulatory system and stimulated to contract during diastole to augment the diastolic blood pressure.

In all of these known procedures, only one channel of neuromuscular stimulation is employed. Therefore, all of the stimulated muscle is activated at one time to contract and compress the blood reservoir within the heart, the aorta or the skeletal muscle ventricle employed in the procedure. Because the entire muscle contracts at the same time, the force of contraction does not propel the blood in a particular direction. Instead, as a result of the contraction, the blood will flow away from the arteries as well as toward the arteries.

The success or failure of a cardiac assistance procedure is judged by measurements of such parameters as cardiac output, ejection fraction, stroke volume, peak pressure, contractility indices and end-diastolic volumes. Results of such examinations to date have shown only minor quantitative improvement resulting from the cardiomyoplasty procedure. (See "The Allegheny Hospital Experience", Magovern G. J. et al., in *Cardiomyoplasty, pp.* 159-170, eds. Carpentier A. et al., Futura, 1991.) One reason for the failure to detect a strong quantitative improvement during a skeletal muscle cardiac assistance procedure may be the failure to direct the flow in a desired direction, toward the arteries.

SUMMARY OF THE INVENTION

The present invention provides for an improved neuromuscular stimulation apparatus and procedure, employing multiple channels of stimulation for the purpose of supplying directional control of blood flow, in addition to the augmentation of the force of contraction which is standard in the art of skeletal muscle cardiac assist devices.

The invention described hereinafter comprises multiple channel stimulation electrodes and a multiple channel cardiosynchronous stimulator to selectively stimulate various sections of the skeletal muscle. The amplitudes of the stimulation pulses and the time delay following a cardiac event may be selected for each channel to appropriately stimulate the muscle to control the order of contraction of particular muscle fibers and thereby to govern the direction of blood flow.

The efficiency of a normal heart as a pump depends on its sequential pattern of excitation and its subsequent contraction to proceed in an orderly and coordinated manner from atria to ventricles.

Conduction of ionic electrical excitation in the heart activates its mechanical pumping action. In a normally beating heart, a continuous progression of excitation proceeds from the sino-atrial node, through the musculature of the atrium, to the atrio-ventricular node and the His bundle, and finally through the muscle of the ventricle. As the wave of electrical excitation passes over the heart from cell to cell, the muscle cells respond by contracting in a continuous wave of contractile force. The electrical action potential precedes the mechanical contraction of the heart muscle. In a properly functioning heart, the action potential first spreads over the atria and then proceeds over the ventricles, progressively recruiting the muscle cells into contraction.

The goal of a skeletal muscle powered cardiac assistance device is to increase the cardiac output of the patient's heart by substituting skeletal muscle for myocardial tissue and to develop the skeletal muscle to operate in the manner of myocardial tissue. Previous known skeletal muscle cardiac assistance procedures and devices have provided for training of skeletal muscle to mimic myocardium by changing the nature of the skeletal muscle from predominantly glycolytic fast-twitch fibers to oxidative slow-twitch fibers which are fatigue-resistant. The present invention also employs conditioning of skeletal muscle to produce fatigue-resistant muscle tissue for assisting the contractility of the heart, but in addition, the present invention stimulates contraction of skeletal muscle in a manner which produces a sequential pattern of excitation, smoothly passing through the muscle tissue, in the form of a wave of contraction. Previously existing skeletal muscle cardiac assistance methods have provided only for stimulation of the skeletal muscle from a single electrode which stimulates all muscle fibers simultaneously to squeeze a reservoir of blood without providing this directional capability.

A controller, which may be a microprocessor, governs the operation of a multiple channel neuromuscular stimulator circuit to determine the timing, intensity and stimulation duration of the pulses applied to a skeletal muscle graft. The stimulation parameters for each channel are set independently of other channels.

A multi-electrode neuromuscular stimulating lead of the present invention incorporates improvements over known implantable leads by providing for multiple separate stimulating electrode elements, electrode elements which are distributed in space within the muscle, and electrode elements that are embedded in a flexible tip. Furthermore, the lead may be employed in a bioelectrical stimulating device for performing neuromuscular stimulation in which the separate, distributed electrode elements may carry stimulating pulses having various, independently set voltage amplitudes, durations and timing. The bioelectrical stimulating device may be programmed using telemetric communication to adapt to the needs of various cardiac assistance applications.

The multiple electrodes in the lead of the present invention may be independently programmed to improve the flexibility of an implanted device. In the application of cardiomyoplasty, neuromuscular stimulation of skeletal muscle is employed to condition the muscle to convert from predominantly a composition of glycolytic fast-twitch muscle fibers to a constitution of oxidative slow-twitch fibers. Conditioning of the muscle results in a significant increase in muscle twitch duration, capillary density and fatigue resistance and a coincident reduction in fusion frequency, the frequency of muscle fiber stimulation leading to a maximum muscle tension.

The response of a single nerve fiber to electrical stimulation depends on the amplitude and duration of the applied electrical stimulation, the position of an electrode with respect to a nerve, the diameter of the stimulated nerve and the nature of the muscle (glycolytic or oxidative) which is stimulated by the nerve. The response of a muscle results from the combined responses of a group of muscle fibers to the stimulation of a group of nerves. As a muscle is conditioned, the coordination of the response to nerve stimulation will change. A bioelectrical stimulating device for performing neuromuscular stimulation provides for telemetric programming of the timing, amplitude and duration of stimulation for each electrode, which allows adaptation to changes in the neuromuscular response of the body with conditioning.

The flexible tip provides a further improvement to the multi-electrode neuromuscular stimulating lead of the present invention because intramuscular electrodes are subject to considerable bending and flexing. A flexible tip allows motion without breaking.

In accordance with one aspect of the present invention, an implantable neuromuscular stimulating apparatus includes multiple channels for stimulating a patient's skeletal muscle which has been surgically prepared to perform cardiac assistance. The apparatus includes a neuromuscular stimulating pulse generator that generates electrical pulses in the multiple channels to stimulate the skeletal muscle in coordination with the patient's cardiac cycle. These electrical pulses are programmed, having a variable intensity, duration and timing. For each of the multiple channels, a first electrode is provided which is adapted to be coupled to excitable tissue in the patient's skeletal muscle. Each of the multiple channels may also have a second ground electrode. Alternatively, a single electrode may serve as ground for all of the multiple channels. A voltage applied between each first electrode and ground provides for stimulation of the skeletal muscle. For each channel, the first electrodes are placed in close proximity to preselected nerve fibers within the patient's skeletal muscle. The neuromuscular stimulating pulse generator applies the pulses to the tissue between the first and second electrodes. The apparatus further includes a controller, which controls the output of the pulse generator to generate electrical pulses in the multiple channels to sequentially excite each channel in a predetermined order, causing the patient's skeletal muscle to contract in a coordinated manner. The controller regulates the operations of the pulse generator by setting variable parameters of pulse intensity, pulse duration, electrical pulse timing, the number of pulses within a stimulation burst and an interpulse interval. The interpulse interval may be constant throughout a burst, or may gradually increment or decrement from one pulse to the next during a burst.

In one application of the present invention, an implantable neuromuscular stimulating apparatus stimulates a patient's skeletal muscle which has been surgically prepared to perform cardiac assistance in a cardiomyoplasty preparation. Here, the patient's latissimus dorsi muscle is wrapped around the heart. The controller within the apparatus further includes a means for determining when the patient's heart is in systole, at which time the controller initiates a stimulation procedure upon the pulse generator by sequentially exciting each subsequent channel of said plurality of channels with an increasing delay with respect to the patient's cardiac cycle such that the skeletal muscle at the apex of the patient's heart contracts first and the contraction proceeds sequentially in the anterior direction. As the controller is increasing the delay for each successive channel, it may decrease the intensity of stimulation.

In a second application of the present invention, an implantable neuromuscular stimulating apparatus stimulates a patient's skeletal muscle in a counterpulsation mode of operation. Here, the skeletal muscle is surgically prepared to perform cardiac assistance in an aortomyoplasty or skeletal muscle ventricle preparation. Here, the patient's latissimus dorsi muscle is wrapped around the aorta or a small diameter cone or cylinder. The controller within the apparatus further includes a means for determining when the patient's heart is in diastole, at which time the controller initiates a stimulation procedure upon the pulse generator by sequentially exciting each subsequent channel of said plurality of channels with an increasing delay with respect to the patient's cardiac cycle such that the skeletal muscle in the proximal portion of the aorta contracts first and the contraction proceeds sequentially in the distal direction. As the controller is increasing the delay for each successive channel, it may decrease the intensity of stimulation.

In accordance with a further aspect of the present invention, body implantable leads conduct electrical stimulating pulses between a bioelectrical stimulating device and electrically excitable tissue in a patient's body. At least one lead includes multiple separate implantable neuromuscular stimulating electrodes having a discharge region firmly positioned with respect to previously determined target nerve branches within the patient's tissue. The bioelectrical stimulating device electrically stimulates these nerve branches by delivering stimulating impulses to the discharge region over a plurality of discrete conductive segments. The stimulation of each segment is independent of the stimulation of any other segment. Each of the plurality of electrical conductor elements has a proximal and a distal end and each is electrically coupled, on its distal end, to one of the discrete conductive segments of the electrodes. Each of the conductor elements is individually electrically insulated. A connector is fixedly attached at the proximal end of the plurality of electrical conductor elements to electrically couple the lead to one or more electrical stimulation generation channels within the bioelectrical stimulating device. The lead also includes a means for inserting at least a portion of the stimulating electrodes conductive segments into the patient's tissue near the nerve branches. This inserting means is fixedly attached near the distal end of the electrical conductor elements.

In accordance with the teachings of another aspect of the present invention, a method of stimulating a patient's skeletal muscle using an implantable neuromuscular stimulating apparatus having a plurality of channels is described. Again, the muscle has been surgically prepared to perform cardiac assistance. The method includes the steps of affixing a first electrode for each of the multiple channels in close proximity to preselected nerve fibers within the patient's skeletal muscle and affixing at least one ground electrode into the skeletal muscle. In one embodiment of the invention, each channel may be provided with a separate ground electrode. In an alternative embodiment, a single ground electrode is provided for all muscle stimulation channels. Subsequently, electrical pulses are generated between the first and ground electrode in each of the multiple channels to stimulate the skeletal muscle in coordination with the patient's cardiac cycle. The electrical pulses may have a variable intensity, duration and timing. The next step is to control the pulse generation step to govern the variable intensity, duration and timing of the electrical pulses in the multiple channels to sequentially excite each channel in a predetermined order, causing the patient's skeletal muscle to contract in a coordinated manner from one portion to another.

In one application of this method, the patient's skeletal muscle surgical preparation is a cardiomyoplasty preparation in which the patient's latissimus dorsi muscle is wrapped around the heart. The controller then determines when the patient's heart is in systole and at that time initiates stimulation. The controller sequentially excites each subsequent channel of the multiple channels with an increasing delay with respect to the patient's cardiac cycle such that the skeletal muscle at the apex of the patient's heart contracts first and the contraction proceeds sequentially in the anterior direction. While sequentially increasing the delay, the controller may decrease the stimulus intensity from one channel to the next.

In a second application of this method, the patient's skeletal muscle surgical preparation is an aortomyoplasty preparation in which the patient's latissimus dorsi muscle is wrapped around the aorta. The controller then determines when the patient's heart is in diastole and at that time initiates stimulation. The controller sequentially excites each subsequent channel of the multiple channels with an increasing delay with respect to the patient's cardiac cycle such that the skeletal muscle in the proximal portion of the aorta contracts first and the contraction proceeds sequentially in the distal direction. While sequentially increasing the delay, the controller may decrease the stimulus intensity from one channel to the next.

DESCRIPTION OF THE DRAWINGS

While the specification concludes with claims particularly pointing out and distinctly claiming the subject matter of the invention, it is believed that the invention will be better understood from the following description, taken in conjunction with the accompanying drawings, in which:

FIG. 15 illustrates one example of cardiac assistance being provided via long-term neuromuscular stimulation of skeletal muscle in an aortomyoplasty application;

FIG. 16 is a graphical depiction of the manner of stimulating the skeletal muscle in an aortomyoplasty application according to the teachings of the present invention;

FIG. 7 illustrates one example of cardiac assistance being provided via long-term neuromuscular stimulation of skeletal muscle in a cardiomyoplasty application;

DETAILED DESCRIPTION OF THE INVENTION

Figure 1:
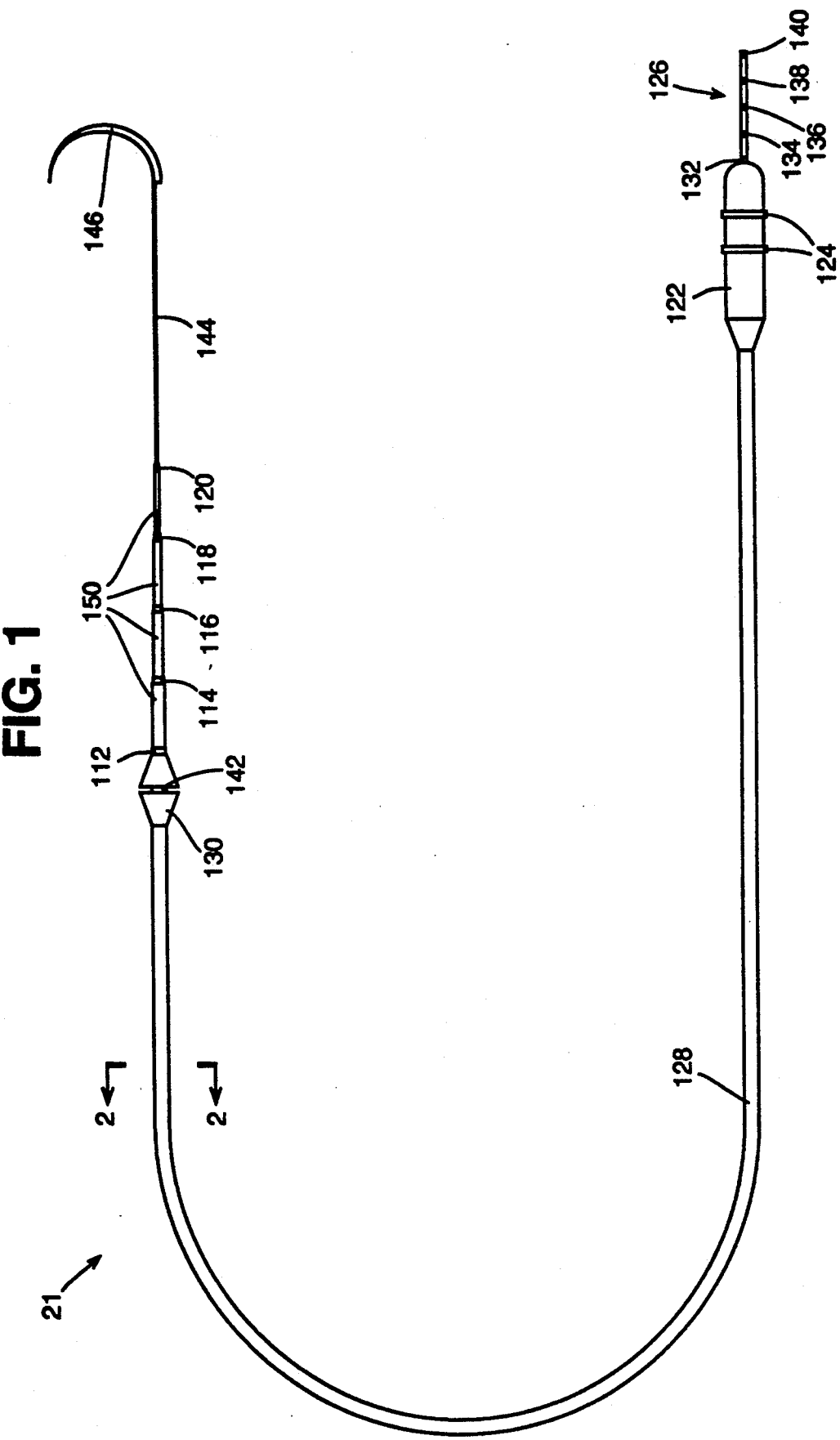
FIG. 1 is an illustration of a chronically implantable lead, in accordance with one embodiment of this invention, for neuromuscular stimulation of surgically adapted skeletal muscle to provide cardiac assistance as part of a bioelectrical stimulating device.
Figure 2:
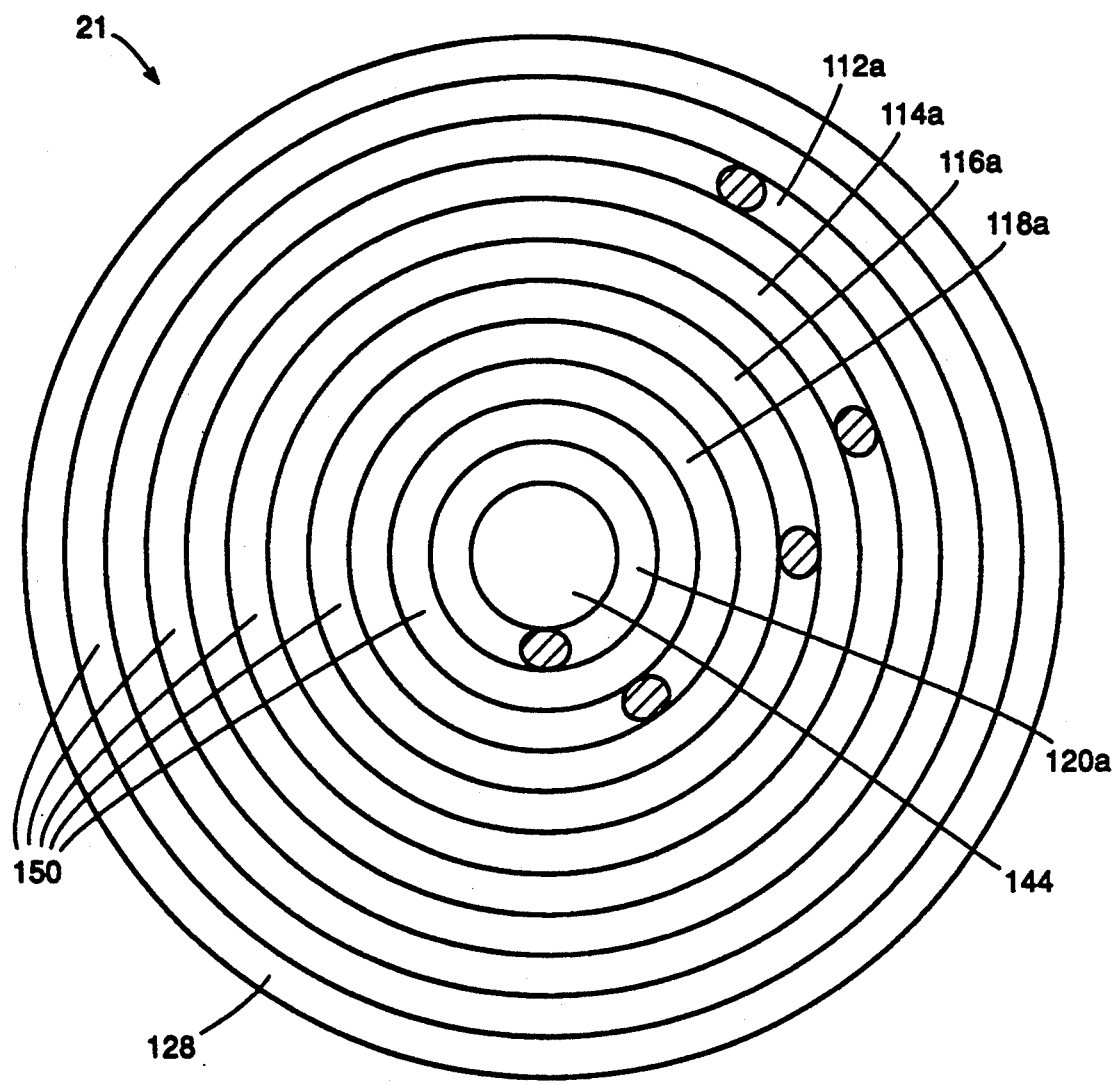
FIG. 2 illustrates a cross-sectional view of the chronically implantable lead, taken along the line 2—2 of FIG. 1.
Figure 3:
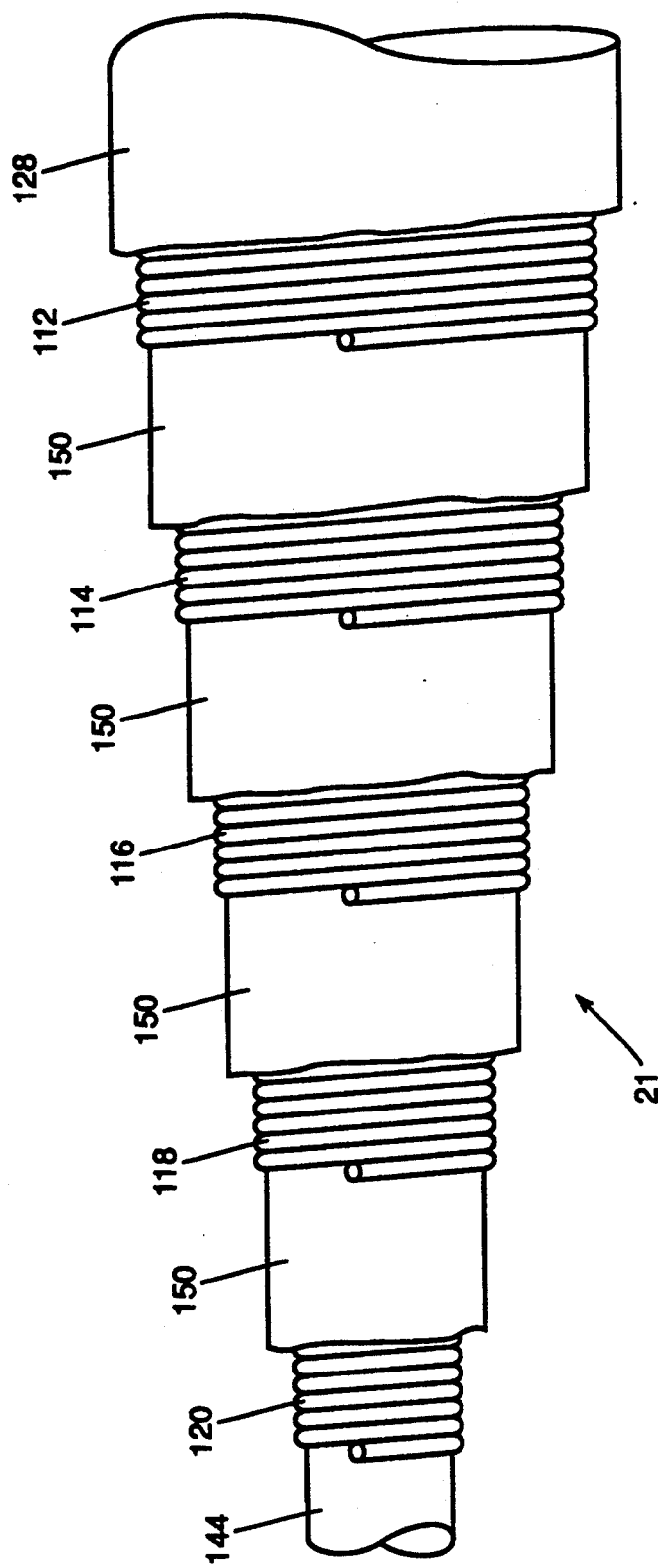
FIG. 3 is an enlarged conceptual side view of a distal end portion of the chronically implantable lead of FIG. 1.

FIGS. 1-3 illustrate a chronically implantable lead 21, which is employed to stimulate surgically adapted skeletal muscle to contract as part of a bioelectrical stimulating device performing neuromuscular stimulation to provide cardiac assistance. A connector 122 is attached to the proximal end portion of the lead 21 to provide coupling between an implantable bioelectrical stimulating device 1 (see FIG. 9) and the lead 21. Two sealing rings 124 are mounted upon the connector 122 to seal the connection between the lead 21 and the implantable bioelectrical stimulating device against intrusion of biological fluids. In the illustrative embodiment of the invention, a terminal 126 includes five terminal pin connector elements 132, 134, 136, 138 and 140 to electrically couple the lead 21 to the implantable bioelectrical stimulating device. Each of the pin connector elements is electrically connected to a corresponding helical conductor within the lead 21 which extends to the distal end portion of the lead, where the insulation 150 surrounding each conductor is broken to form an electrode. Thus, electrodes 112, 114, 116, 118 and 120 are electrically connected with terminal pin connector elements 132, 134, 146, 138 and 140 via conductors 112a, 114a, 116a, 118a and 120a, respectively. An insulating sheath 128 provides electrical insulation to the lead 21, preventing electrical currents from flowing between the lead 21 and body fluids. Each conductor within the lead 21 is also individually insulated. A transition sleeve 130 marks the boundary between the insulated portion 128 of the lead 21 and the distal electrically conductive electrode portion of the lead 21. Electrodes 112, 114, 116, 118 and 120 are portions of the conductors in lead 21, which make electrical contact to biological tissue by virtue of a break in the individual insulation of each conductor. Electrodes 112, 114, 116, 118 and are composed of platinum or a platinum iridium alloy. Furthermore, the insulating sheath 128 does not extend to the region of the lead 21 in the vicinity of the electrodes. Upon implantation of the lead 21, imbedded sutures located within a notch 142 in the suture sleeve 130 may be used to secure the lead.

A suture strand 144, made of a polymer material such as polypropylene, is affixed to the lead and extends from its proximal end throughout the length of the lead to the distal end of the lead, where it is attached to an insertion needle 146. The suture strand 144 is situated within the center of the lead 21.

As best seen in FIGS. 2 and 3, helical conductor 120a encircles the suture strand 144 and terminates in the electrode 120 at the distal end of the lead 21, where the insulating polymer material 150 enveloping the conductor is broken. Similarly, helical conductor 118a overlies the insulating material covering the electrode 120 and comprises the electrode 118 at the distal end portion of the lead 21. In a like manner, a cylindrical layer of insulating polymer material 150 overlies the conductor for the electrode 118. The remaining helical conductors 116a, 114a and 112a, which terminate in the electrodes 116, 114 and 112, respectively, are each separated and overlaid by a cylinder of insulating polymer material 150. Overlying each of the concentric cylindrical layers of conductors and insulating material is the insulating sheath 128. At the distal end of the lead 21, the insulating sheath 128 and the outer layer of the insulating polymer material 150 do not extend beyond the suture sleeve 130 (shown in FIG. 1), exposing the outer conductor to provide the electrode 112. Beyond the electrode 112 the insulating material 150 underlying conductor 112a tapers distally to the next interior conductor 144a that is exposed to provide the electrode 114. The insulating material 150 underlying each successive conductor 114a, 116a and 118a tapers distally to the next interior conductor cylinder, exposing electrodes 116, 118 and 120, respectively. Alternatively, the insulated helical conductors 112a, 114a, 116a, 118a and 120a may extend and electrically couple to corresponding conductive cylindrical sleeves (not shown), or other conductive elements, which serve as electrodes 112, 114, 116, 118 and 120.

Figure 4:
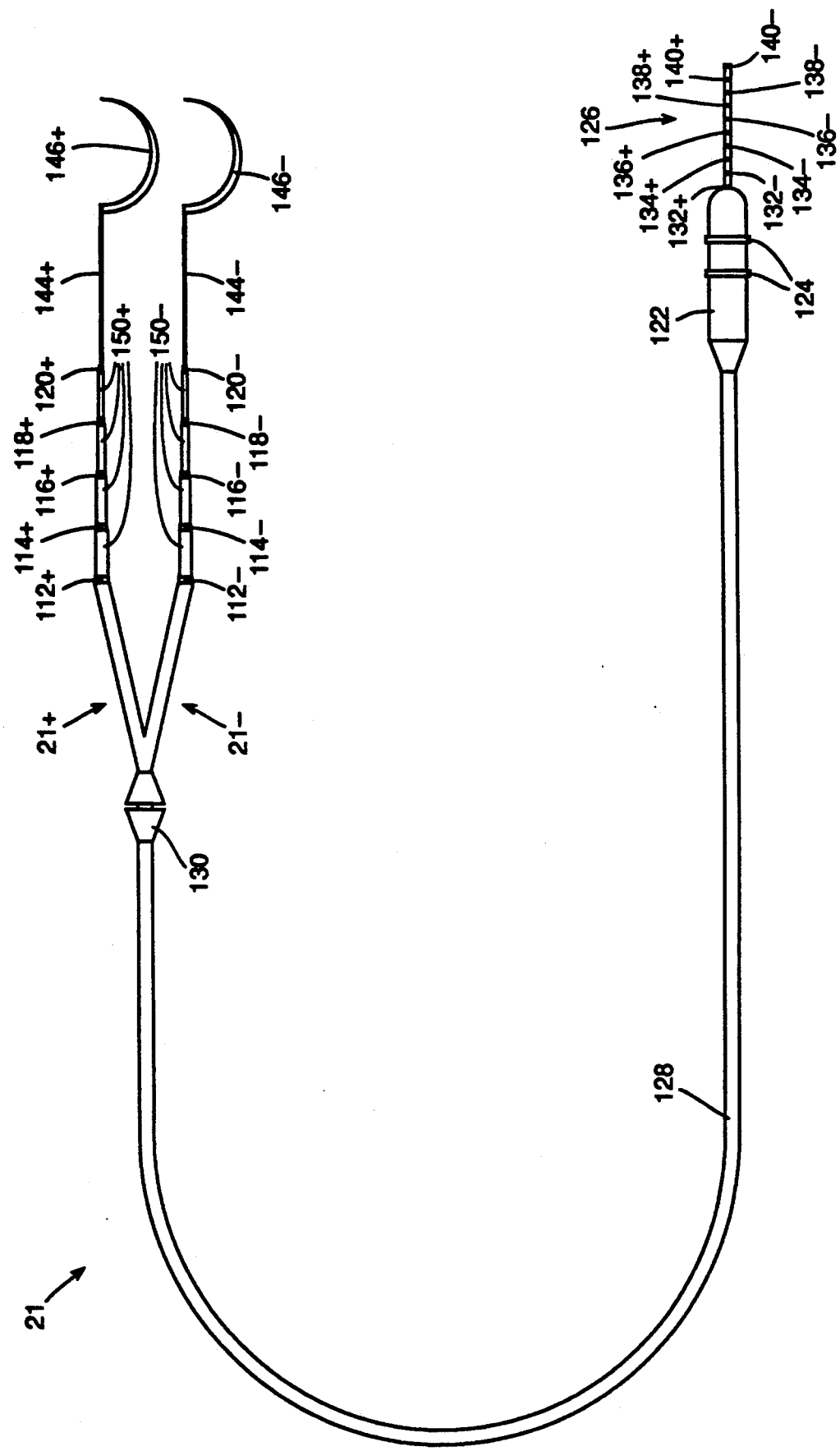
FIG. 4 is an illustration of an embodiment of a chronically implantable lead for neuromuscular stimulation of surgically adapted skeletal muscle, in which the lead includes both positive and negative electrodes for each channel.

FIG. 4 is an illustration of a chronically implantable lead 21, which is similar to the lead of FIG. 1 but provides for both negative and positive electrodes for each channel, which electrodes are positioned in respective negative and positive distal portions 21− and 21+ of the lead. Similar to FIG. 1, a connector 122 is attached to the proximal end of the lead 21 to provide coupling between an implantable bioelectrical stimulating device 1 (FIG. 9) and the lead 21. Two sealing rings 124 are mounted upon the connector 122 to seal the connection between the lead 21 and the implantable bioelectrical stimulating device. A terminal 126 includes ten terminal pin connector elements 132+, 132−, 134+, 134−, 136+, 136−, 138+, 138−, 140+ and 140− to electrically couple the lead 21 to the implantable bioelectrical stimulating device. Each of the pin connector elements is electrically connected to a corresponding conductor (not shown) within the lead 21 which extends to the distal end of the lead, where the insulation 150+ and 150− for each conductive element is broken to form an electrode. Thus, electrodes 112+, 112−, 114+, 114−, 116+, 116−, 118+, 118−, 120+ and 120− are electrically connected with terminal pin connector elements 132+, 132−, 134+, 134−, 136+, 136−, 138+, 138−, 140+ and 140−, respectively. An insulating sheath 128 provides electrical insulation to the lead 21. Each conductor within the lead 21 is also individually insulated. A transition sleeve 130 marks the boundary between the insulated portion 128 of the lead and the distal electrically conductive electrode portion of the lead 21. Electrodes 112+, 121−, 114+, 114−, 116+, 116−, 118+, 118−, 120+ and 120− are portions of the conductors in lead 21, which make electrical contact to biological tissue by virtue of a break in the individual insulation of each conductor. The electrodes are composed of platinum or a platinum iridium alloy.

Figure 5:
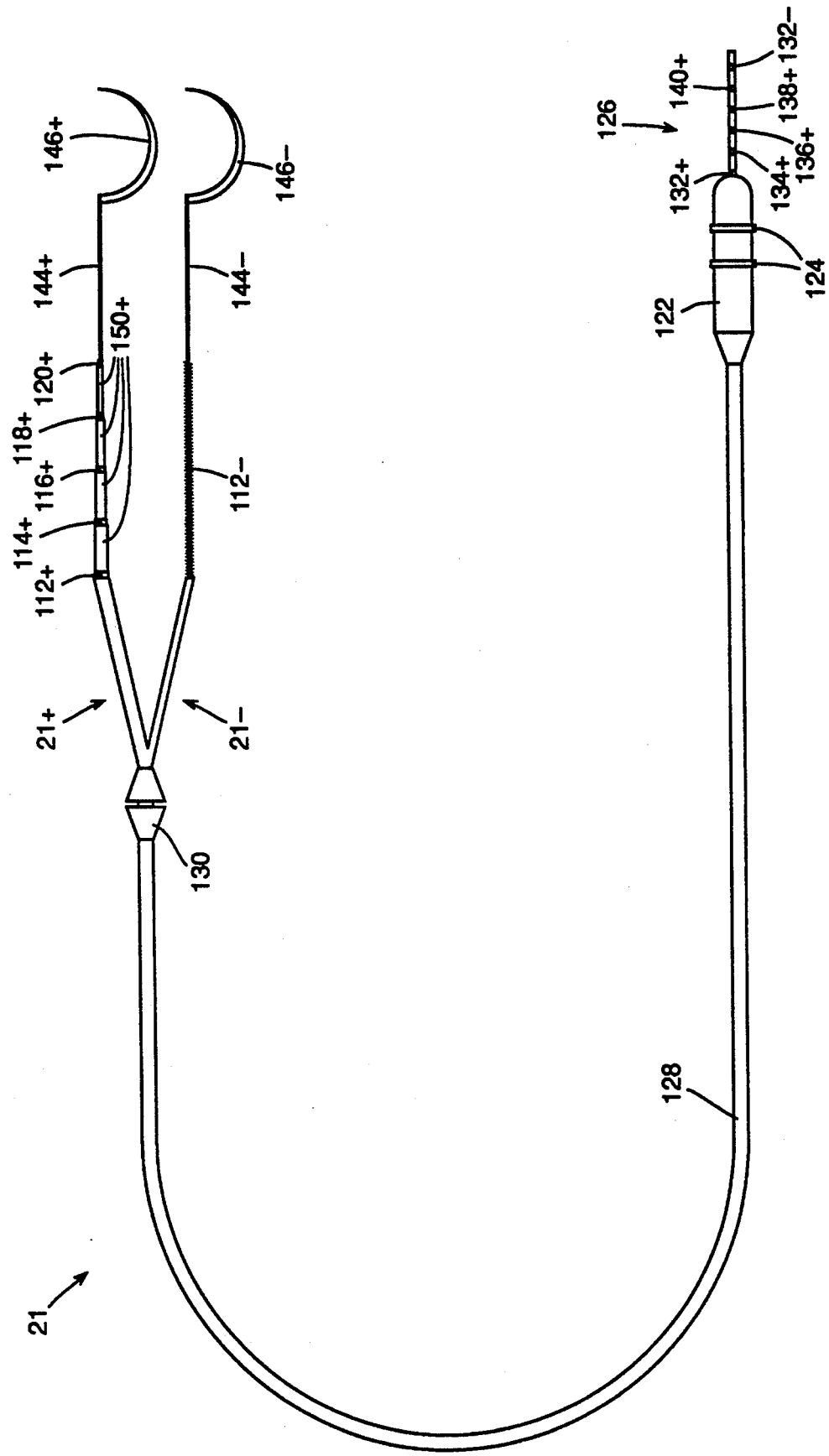
FIG. 5 is an illustration of another embodiment of a chronically implantable lead for neuromuscular stimulation of surgically adapted skeletal muscle, in which the lead includes a positive electrode for each channel and a single negative electrode which is shared by the channels.

FIG. 5 is an illustration of a chronically implantable lead 21, which is similar to the lead of FIG. 4 but provides for a single negative electrode 112−, positioned in the negative distal portion 21− of lead 21, that is shared by all channels. Similar to FIG. 4, a connector 122 is attached to the proximal end of the lead 21 to provide coupling between an implantable bioelectrical stimulating device 1 (FIG. 9) and the lead 21. Two sealing rings 124 are mounted upon the connector 122 to seal the connection between the lead 21 and the implantable bioelectrical stimulating device. A terminal 126 includes six terminal pin connector elements 132+, 134+, 136+, 138+, 114+ and 132− to electrically couple the lead 21 to the implantable bioelectrical stimulating device. Each of the pin connector elements is electrically connected to a corresponding conductor within the lead 21 which extends to the distal end of the lead, where the insulation 150 for each conductive element is broken to form an electrode. Thus, electrodes 112+, 112−, 114+, 116+, 118+ and 120+ are electrically connected with terminal pin connector elements 132+, 132−, 134+, 136+, 138+ and 140+, respectively. An insulating sheath 128 provides electrical insulation to the lead 21. Each conductor within the lead 21 is also individually insulated. A transition sleeve 130 marks the boundary between the insulated portion 128 of the lead 21 and the distal electrically conductive electrode portion of the lead 21. Electrodes 112+, 112−, 114+, 116+, 118+, and 120+ are portions of the conductors in lead 21 which make electrical contact to biological tissue by virtue of a break in the individual insulation of each conductor. The electrodes are composed of platinum or a platinum iridium alloy.

Figure 6:
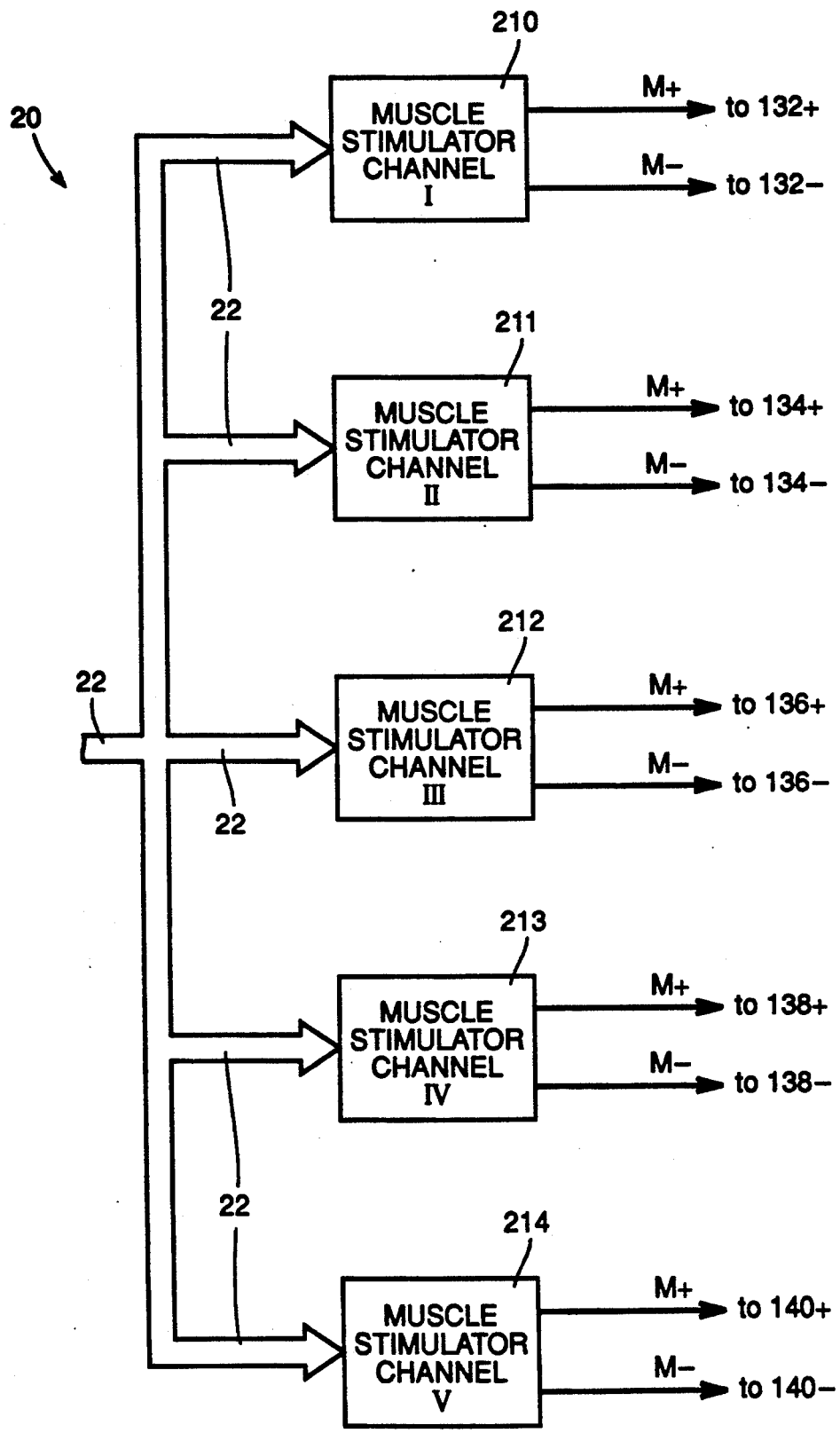
FIG. 6 depicts a block diagram of a five channel skeletal muscle stimulator circuit for generating electrical stimulation pulses on the lead of FIG. 4.

FIG. 6 depicts a block diagram of a five channel skeletal muscle stimulator 20 for electrically driving the electrodes 112+, 112−, 114+, 114−, 116+, 116−, 118+, 118−, 120+ and 120− in lead 21 of FIG. 4. The five channel skeletal muscle stimulator 20 would supply stimulating voltages for two identical leads 21, corresponding to the positive and negative lead portions 21+ and 21− of FIG. 4, if the stimulator is connected with leads such as those illustrated in FIG. 1. The electronic circuits for muscle stimulator channels I through V, blocks 210, 211, 212, 213 and 214, respectively, are identical, as disclosed in the drawing and description of FIG. 7, hereinafter. The skeletal muscle stimulator 20 receives input signals from a microprocessor 19 (FIG. 9) over a skeletal muscle stimulation control bus 22. These signals designate the channel to be activated, as well as the amplitude, timing and polarity of the stimulus pulses to be generated. Muscle stimulator channel I 210 generates neuromuscular stimulating pulses that drive the terminal pin connector elements 132+ and 132−, which activate the electrodes 112+ and 112− in lead 21. Likewise, muscle stimulator channel II 211 drives terminal pin connector elements 134+ and 134− and electrodes 114+ and 114−, muscle stimulator channel III 212 drives terminal pin connector elements 136+ and 136− and electrodes 116+ and 116−, muscle stimulator channel IV 213 drives terminal pin connector elements 138+ and 138− and 118+ [and 118−, and muscle stimulator channel V 214 drives terminal pin connector elements 140+ and 140− and electrodes 120+ and 120−.

Figure 7:
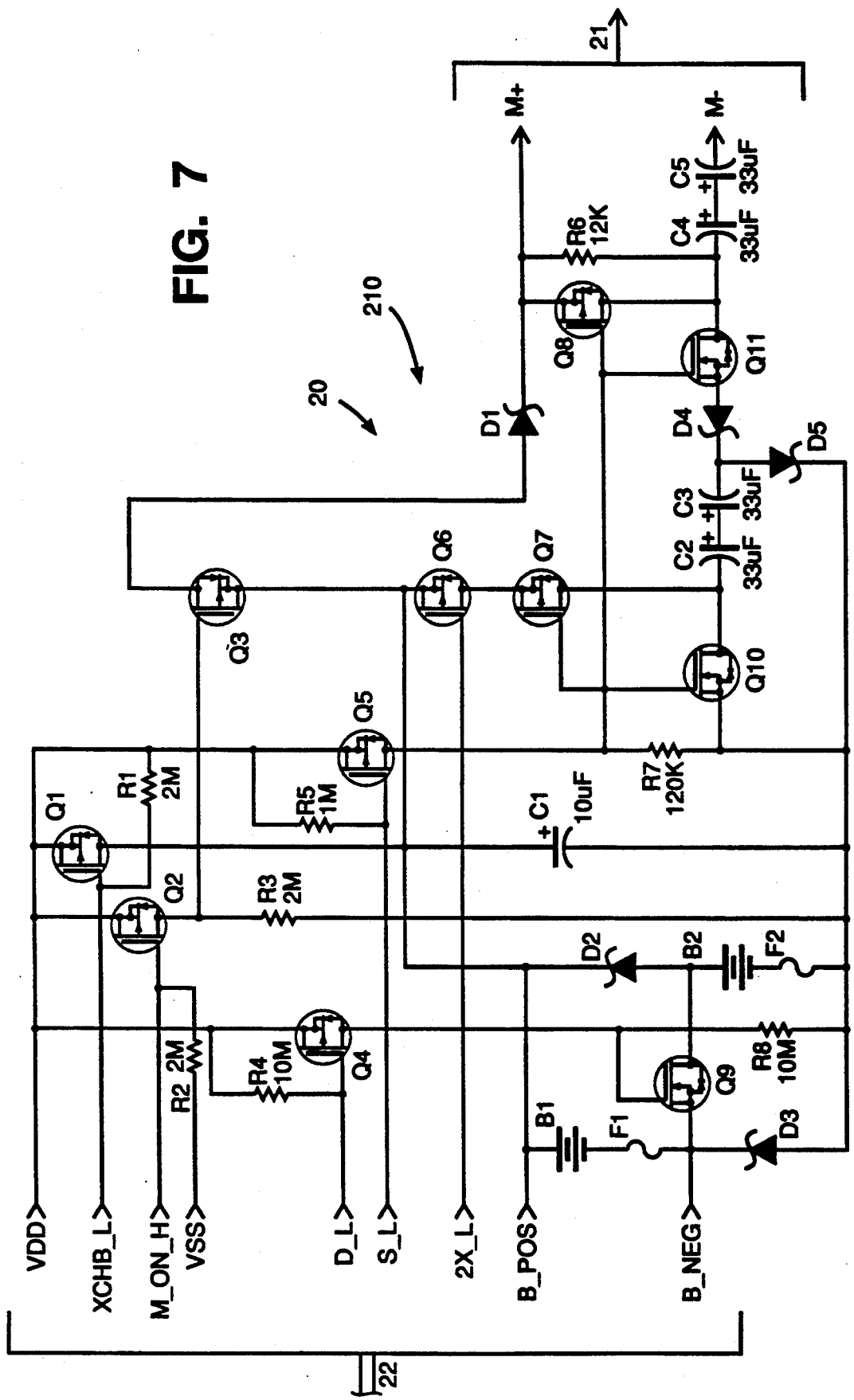
FIG. 7 illustrates a circuit schematic of a single channel of a skeletal muscle stimulator capable of electrically driving the implantable leads of FIGS. 4 and 5.

FIG. 7 illustrates a circuit schematic of one channel of the five channel skeletal muscle stimulator 20, for example channel I 210, which electrically drives electrodes 112+ and 112− of FIG. 4. Each channel of skeletal muscle stimulator 20 receives input signals from microprocessor 19 over skeletal muscle stimulation control bus 22. These signals include a power input VDD, which is typically an amplitude of 2.8 V, and a ground reference VSS, as well as control signals S_L, 2X_L, D_L, XCHB_L and M$_{13}$ON_H. A pacemaker 17 (FIG. 9) supplies battery power B_POS and B_NEG which provides energy for biphasic skeletal muscle stimulation. In the preferred embodiment of the present invention, the B_POS amplitude is about 3 V. The battery voltages B_POS and B_NEG are floating with respect to circuit power VDD to prevent variations in circuit energy during different parts of the cardiac cycle caused by inconsistent demands on the battery from the pacing pulse and skeletal muscle stimulation pulse generation circuits.

XCHB_L, a cross channel blanking control signal from the microprocessor 19, is also supplied to a sense blanking input (not shown) of the pacemaker 17 to disable pacemaker sensing during generation of a skeletal muscle stimulation pulse. This prevents the pacemaker 17 from incorrectly classifying a skeletal muscle stimulation pulse as an episode of intrinsic cardiac activity.

The circuit of FIG. 7, in response to codes written from the microprocessor 19, produces biphasic skeletal muscle stimulation pulses on the skeletal muscle lead, M+ and M−. Biphasic cathodic pulses are preferred to monophatic pulses to minimize electrochemical damages at the electrode site. All characteristics of the skeletal muscle stimulation pulses—the timing, frequency, burst duration, amplitude, pulse width, and pulse morphology—are determined by the microprocessor. FIG. 7 circuitry merely responds to these input codes by producing a particular amplitude and polarity signal on the M+ and M− leads. In this manner, the microprocessor generates the characteristics of the skeletal muscle stimulation pulses according to the timing of codes written to the skeletal muscle stimulation control bus 22.

Input signal lines S_L, M_ON_H and XCHB_L contain skeletal muscle pulse enable and polarity control signals which are dynamic in the sense that the microprocessor 19 defines the code to be written and the time duration that a particular code will be sustained, writes the codes to the skeletal muscle stimulation control bus 22, writes predetermined time duration information to a timer within the processor (timer I, 51, or timer II, 52, of FIG. 11), waits for a timer wakeup and initiates the next code. The microprocessor enables the circuit of FIG. 7 to produce an output on one or the other of leads M+ and M− by setting input signal line M_ON_H to "1" which, by means of control by p-channel switching field effect transistor Q3, applies either B_POS or B_NEG battery power to the corresponding leads M+ and M−, depending on the signal on input signal line S_L. The microprocessor controls the stimulus pulse timing and width by setting a signal on input signal line S_L for a predetermined time and duration.

Figure 8:
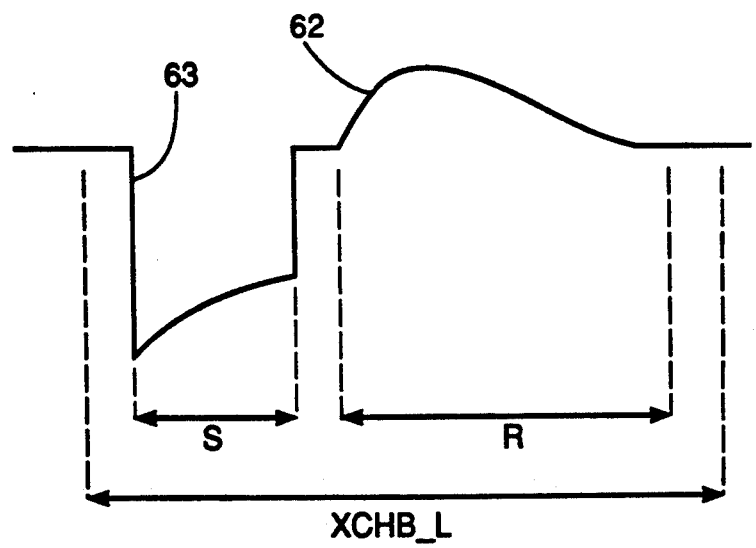
FIG. 8 depicts the form of a biphasic skeletal muscle stimulation pulse generated by the circuit of FIG. 7.

When microprocessor 19 writes a "0" value to input signal line S_L while a "1" value is on input signal line M_ON_H, the outputs of p-channel switching field effect transistors Q7 and Q8 are enabled to enable the M+ lead, and the outputs of n-channel switching field effect transistors Q10 and Q11 are disabled to disable the M− lead, producing a positive polarity output pulse on the lead M+, having a duration R, as shown at 62 in FIG. 8. The stimulus duration R is a programmable parameter for the microprocessor. Alternatively, the microprocessor ay write a "1" value to line S_L to disable field effect transistors Q7 and Q8 and enable transistors Q10 and Q11, while a "1" value is on line M_ON_H, to produce a negative polarity output pulse on the lead M−, having a duration S, as shown at 63 in FIG. 8. The stimulus duration S is a programmable parameter for the microprocessor. If the value applied to input signal line M_ON_H is "0", neither lead M+ nor lead M− are energized and the skeletal muscle stimulator does not produce a pulse.

As indicated earlier, microprocessor 19 controls cross blanking control signal line XCHB_L to set the timing and duration of the sense blanking input to the pacemaker 17 in order to disable pacemaker sensing during generation of a skeletal muscle stimulation pulse. Cross channel blanking duration may be a programmable parameter for the microprocessor.

In an embodiment of the invention in which the lead 21 has multiple positive electrodes 112+, 114+, 116+, 118+ and 120+, and only a single negative electrode 112− (see FIG. 5) is attached to a bioelectrical device having multiple channels (see FIG. 7), all of the negative channels (M−) of the circuit are connected with the common negative terminal pin connector 132− of terminal 126. In this case the microprocessor 19 is programmed so that only a single negative channel M− of the multiple channels may be energized at one time.

Input signal lines D_L and 2X_L contain skeletal muscle pulse amplitude control signals which are static in the sense that microprocessor 19 writes them, at most, only once per cycle. Normally, the microprocessor only writes amplitude control signals upon reprogramming, via telemetry, by an external communicating device. Line D_L is utilized as a battery voltage doubler. Line 2X_L is utilized as a stimulus voltage doubler. Thus, lines D_L and 2X_L remain at the same settings throughout numerous cardiac cycles, while the skeletal muscle pulse that is generated has a negative, positive or zero polarity. When the microprocessor sets line D_L to "1" ("on"), the n-channel switching field effect transistor Q enables doubling of the battery voltage. In a similar manner (but with an opposite polarity), when the microprocessor sets line 2X_L to "0" ("on"), the p-channel switching field effect transistor Q9 enables doubling of the stimulus voltage. Therefore, when the microprocessor sets line D_L "off" (1) and line 2X_L "off" (1), the amplitude of the skeletal muscle stimulation pulse is equal to the battery voltage, 3 V in the preferred embodiment of the invention. When the microprocessor sets line D_L "on" ("1") and line 2X_L "off" ("1"), the amplitude of the skeletal muscle stimulation pulse is equal to twice the battery voltage (6 V). When the microprocessor sets line D_L "on" ("1") and line 2X_L "on" ("0"), the amplitude of the skeletal muscle stimulation pulse is equal to four times the battery voltage (12 V).

Figure 9:
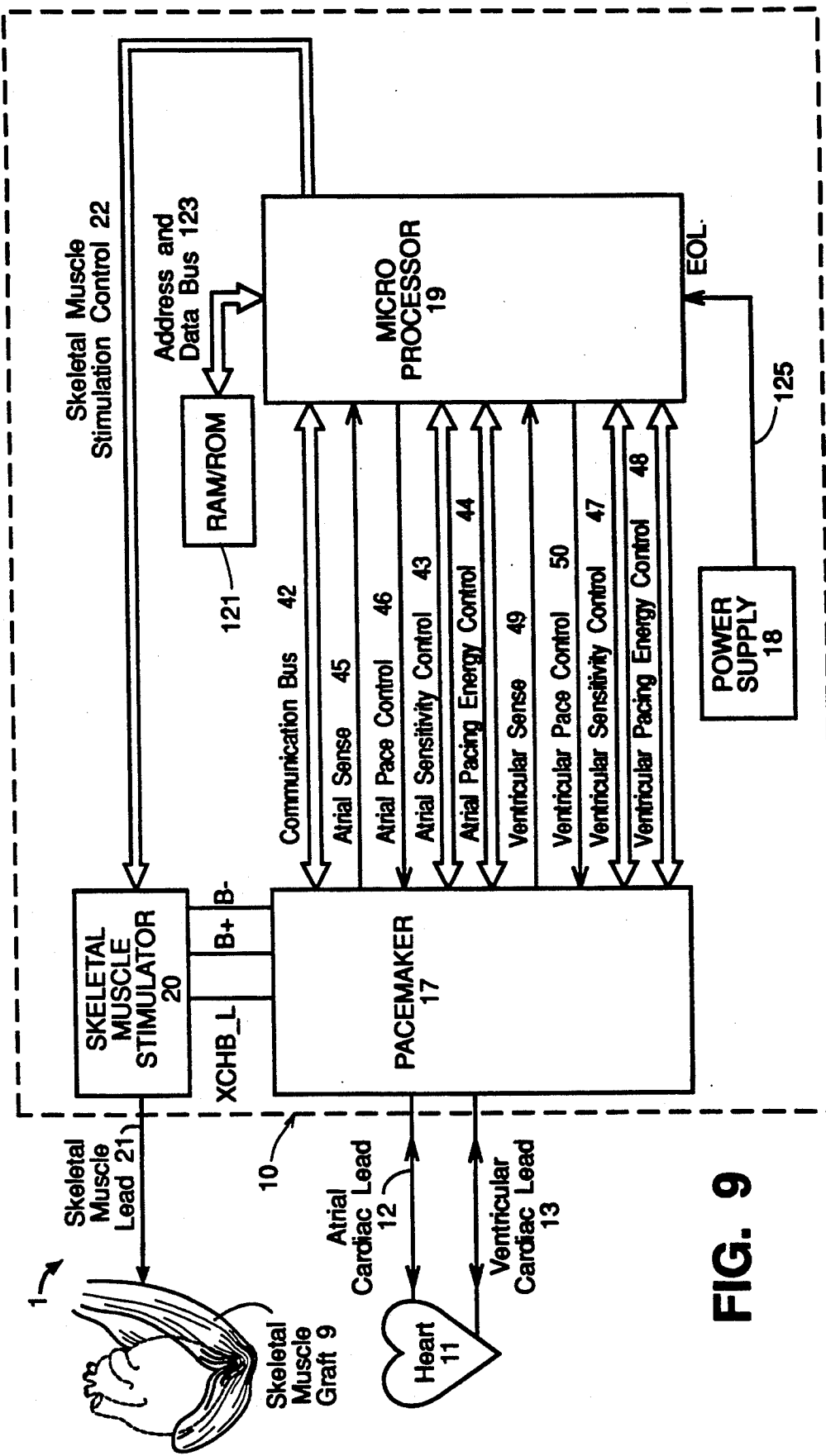
FIG. 9 is a block diagram of an implanted bioelectrical stimulating device in accordance with the present invention.

Referring to FIG. 9, when the microprocessor 19 determines that skeletal muscle graft stimulation is appropriate, it works in conjunction with the skeletal muscle stimulator 20 to produce pulses or bursts of pulses, which are applied to the skeletal muscle graft 9. The microprocessor may time these pulses or bursts of pulses with respect either to intrinsic or to paced cardiac activity which is sensed or generated, respectively, by the pacemaker 17. This mode of skeletal muscle stimulation is termed "synchronous" skeletal muscle stimulation. Alternatively, the microprocessor 19 may time the pulses or bursts of pulses according to the operations of an internal timer, wherein the stimulation occurs asynchronously with respect to individual cardiac events.

According to "synchronous" programming of the microprocessor 19, when the pacemaker 17 detects either a natural atrial or a natural ventricular intrinsic event it will send a signal to the microprocessor 19 via atrial sense line 45 or ventricular sense line 49. The microprocessor 19 may be programmed to respond to such a signal by generating skeletal muscle stimulation. Alternatively, in the event that the patient's natural heart rate falls below a predetermined rate, then the microprocessor will send an atrial pace control signal on line 46, a ventricular pace control signal on line 50, or both signals, to the pacemaker 17 to generate a pacing pulse to the heart. In addition, the microprocessor 19, may be programmed to trigger skeletal muscle stimulation after such a pacing event.

Programming of synchronous operation of the skeletal muscle stimulator includes the specification of a synchronization ratio which determines the ratio of cardiac events for each skeletal muscle stimulation burst. The microprocessor 19 resets a cardiac event counter with each initiation of a skeletal muscle stimulation burst and increments the counter with each subsequent cardiac event. For each skeletal muscle stimulation burst, the microprocessor 19 waits a predetermined and programmed delay interval before initiating the burst.

Other programmed parameters which may be utilized are an interpulse interval (the time between sequential pulses), the stimulus duration, the recharge duration, the cross-channel blanking duration and a maximum muscle stimulation rate. All or some of these parameters may have preprogrammed sets of values which depend on the rate at which the heart is beating. An interpulse interval determines the time intervals between each individual pulse within a burst of pulses. A burst frequency is the reciprocal of the interpulse interval. The maximum muscle stimulation rate is an upper rate boundary of synchronization of cardiac and muscle stimulation activity. Upon a cardiac event occurring at cardiac rates faster than the maximum muscle stimulation rate, the microprocessor will fail to generate skeletal muscle stimulation but will, instead, stimulate the skeletal muscle based upon triggering by the next subsequent cardiac event.

Referring to FIG. 9, there is depicted a block diagram of a bioelectrical stimulating device 1. Device 1 is designed to be implanted within a patient and includes a pulse module 10 and appropriate leads for connecting module 10 to a patient's heart 11. More particularly, device 1 may include an atrial cardiac lead 12 extending to the atrium of the patient's heart for the administration of therapy to the atrium, and generally will include a ventricular cardiac lead 13 extending to the ventricle of the patient's heart for the administration of therapy to the ventricle. Device 1 generally also includes a pacemaker 17 for the detection of analog signals representing cardiac electrical activity and for the delivery of pacing pulses to the heart; a microprocessor 19 which, in response to various inputs received from the pacemaker 17, performs various operations so as to generate different control and data outputs to pacemaker 17 and to skeletal muscle stimulator 20; and a power supply 18 for the provision of a reliable voltage level to pacemaker 17, microprocessor 19 and skeletal muscle stimulator 20 by suitable electrical conductors (not shown). Skeletal muscle stimulator 20 generates electrical pulses on a skeletal muscle lead 21 for stimulating a skeletal muscle graft 9, such as a patient's latissimus dorsi muscle, according to timed control signals from microprocessor 19 communicated via skeletal muscle stimulation control bus 22.

Microprocessor 19 is connected to a random access memory/read only memory (RAM/ROM) unit 121 by an address and data bus 123. An end-of-life (EOL) signal line is used to provide, to microprocessor 19, a logic signal indicative of the approach of battery failure in power supply 18. As more fully described below, microprocessor 19 and pacemaker 17 are connected by a communication bus 42, the atrial sense line 45, the atrial pace control line 46, an atrial sensitivity control bus 43, an atrial pacing energy control bus 44, the ventricular sense line 49, the ventricular pace control line 50, a ventricular sensitivity control bus 47, and a ventricular pacing energy control bus 48. Microprocessor 19 transmits control signals, according to the description below, over skeletal muscle stimulation control bus 22 to the skeletal muscle stimulator 20.

Figure 10:
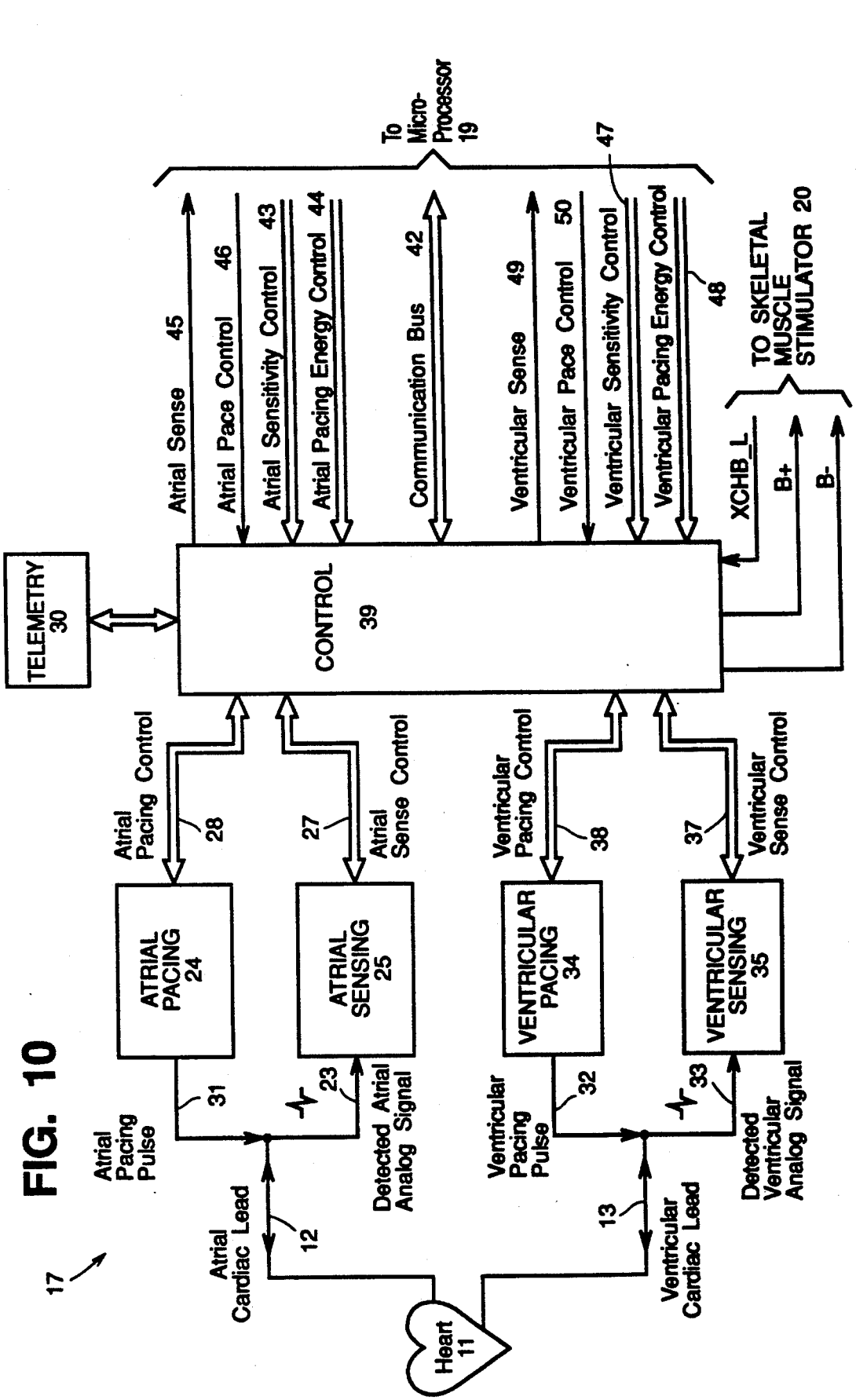
FIG. 10 is a block diagram of a pacemaker utilized in the device of FIG. 9.

Referring to FIG. 10, pacemaker 17 comprises circuitry for atrial pacing 24, ventricular pacing 34, atrial sensing 25, ventricular sensing 35, and telemetry 30. In addition, pacemaker 17 includes a control block 39 which includes an interface to microprocessor 19.

In Operation, sensing circuits 25 and 35 detect respective atrial and ventricular analog signals 23 and 33 from the heart 1 and convert the detected signals to digital signals. In addition, the sensing circuits 25 and 35 receive an input atrial sense control 27 and an input ventricular sense control 37, respectively, from the control block 39 which determines the sensitivity applied to the detection circuit.

Atrial pacing circuit 24 receives from control block 39, via an atrial pacing control bus 28, an atrial pace control input and an atrial pacing energy control input. Similarly, ventricular pacing circuit 34 receives from control block 39, via a ventricular pacing control bus 38, a ventricular pace control input and a ventricular pacing energy control input. The atrial and ventricular pace control inputs determine the respective types of atrial and ventricular pacing to be delivered to the heart via an atrial pacing pulse lead 31 and atrial cardiac lead 12, and Via a ventricular pacing pulse lead 32 and ventricular cardiac lead 13, respectively. The atrial and ventricular pacing energy control inputs determine the respective magnitudes of the pacing pulse energy so delivered.

Telemetry circuit 30 provides a bidirectional link between control block 39 of pacemaker 17 and an external device such as a programmer (not shown). It allows data such as the operating parameters to be read from or altered in the implanted module 10.

Figure 11:
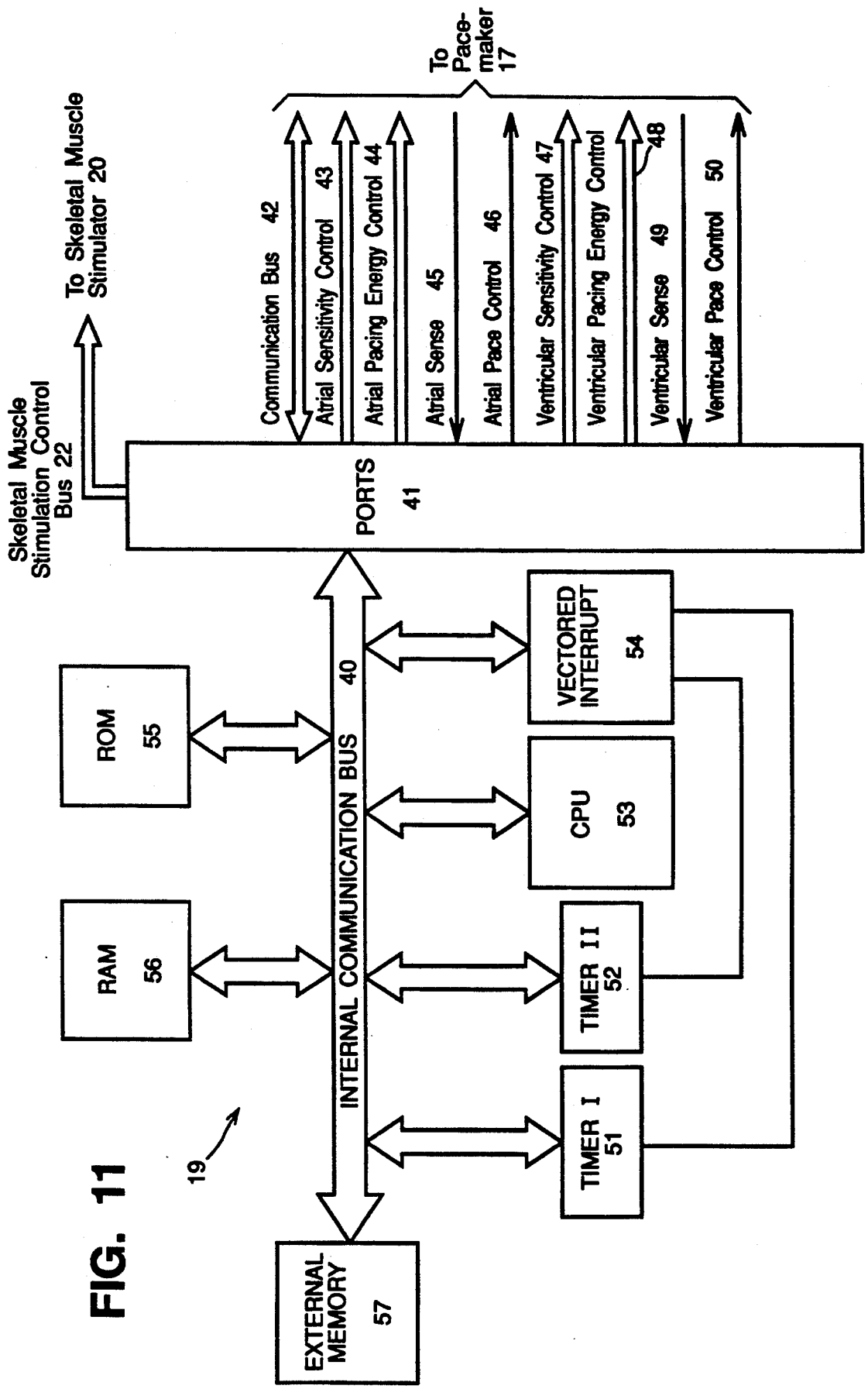
FIG. 11 is a block diagram of a microprocessor utilized in the device of FIG. 9.

Referring to FIG. 11, microprocessor 19 comprises two 16-bit timers 51 and 52, a CPU 53, a vectored interrupt block 54, a ROM 55, a RAM 56, an external memory 57, a ports block 41 and an internal communication bus 40. RAM 56 acts as a scratch pad and active memory during execution of the various programs stored in ROM 55 and used by microprocessor 19. These programs include system supervisory programs and neuromuscular stimulation control programs, as well as storage programs for storing, in external memory 57, data concerning the functioning of module 10 and the electrogram provided by ventricular cardiac lead 13 (FIG. 9). Timers 5 1 and 52, and associated control software, implement some timing functions required by microprocessor 19 without resort entirely to software, thus reducing computational loads on and power dissipation by CPU 53.

Signals received from telemetry circuit 30 (FIG. 10) permit an external programmer (not shown) to change the operating parameters of pacemaker 17 by supplying appropriate signals to control block 39. Communication bus 42 serves to provide signals indicative of such control to microprocessor 19. Thus, it is also possible for an external programmer to control operation of the skeletal muscle stimulator 20 by means of signals provided to microprocessor 19.

Appropriate telemetry commands may cause telemetry circuit 30 to transmit data to the external programmer. Data stored is read out, by microprocessor 19, on to communication bus 42, through control block 39 in pacemaker 17, and into telemetry circuit 30 for transmission to the external programmer by a transmitter (not shown) in telemetry circuit 30.

Microprocessor 19 receives various status and/or control inputs from the pacemaker 17, such as the sense signals on sense lines 45 and 49. It performs operations, such as neuromuscular stimulation timing and amplitude control functions, and produces outputs, such as the atrial pace control on line 46 and the ventricular pace control on line 50, which determine the type of pacing that is to take place. Other control outputs generated by microprocessor 19 include the atrial and ventricular pacing energy controls on buses 44 and 48, respectively, which determine the magnitude of the pulse energy, and the atrial and ventricular sensitivity controls on buses 43 and 47, respectively, which determine the sensitivity settings of the sensing circuits. In addition, the microprocessor 19 controls all aspects of skeletal muscle stimulation, as will be described in detail below, by formulating control signals and transmitting these signals over the skeletal muscle stimulation control bus 22 to skeletal muscle stimulator 20.

The effectiveness of the cardiac assistance provided by neuromuscular stimulation of the skeletal muscle graft 9 (FIG. 9) may be measured by diagnostic tests, including electrocardiogram monitoring, two dimensional and Doppler echocardiography, nuclear medicine multigated scan procedures employing radioisotopes such as technetium 99m, and measurements of oxygen uptake during exercise. As a health care practitioner performs one or more of these diagnostic tests, neuromuscular stimulation parameters may be altered via telemetry to achieve the highest degree of cardiac assistance. For example, during an early conditioning phase of the skeletal muscle graft 9, low-amplitude stimulation pulses are applied infrequently and a steady stimulation of the different channels is employed to activate the skeletal muscle without generating large current flows in the muscle. Later, as the muscle becomes conditioned, the stimulating procedure may be tested and varied to determine an optimum stimulation procedure, which depends on the relative location of the electrodes with respect to the muscle innervation.

Figure 12:
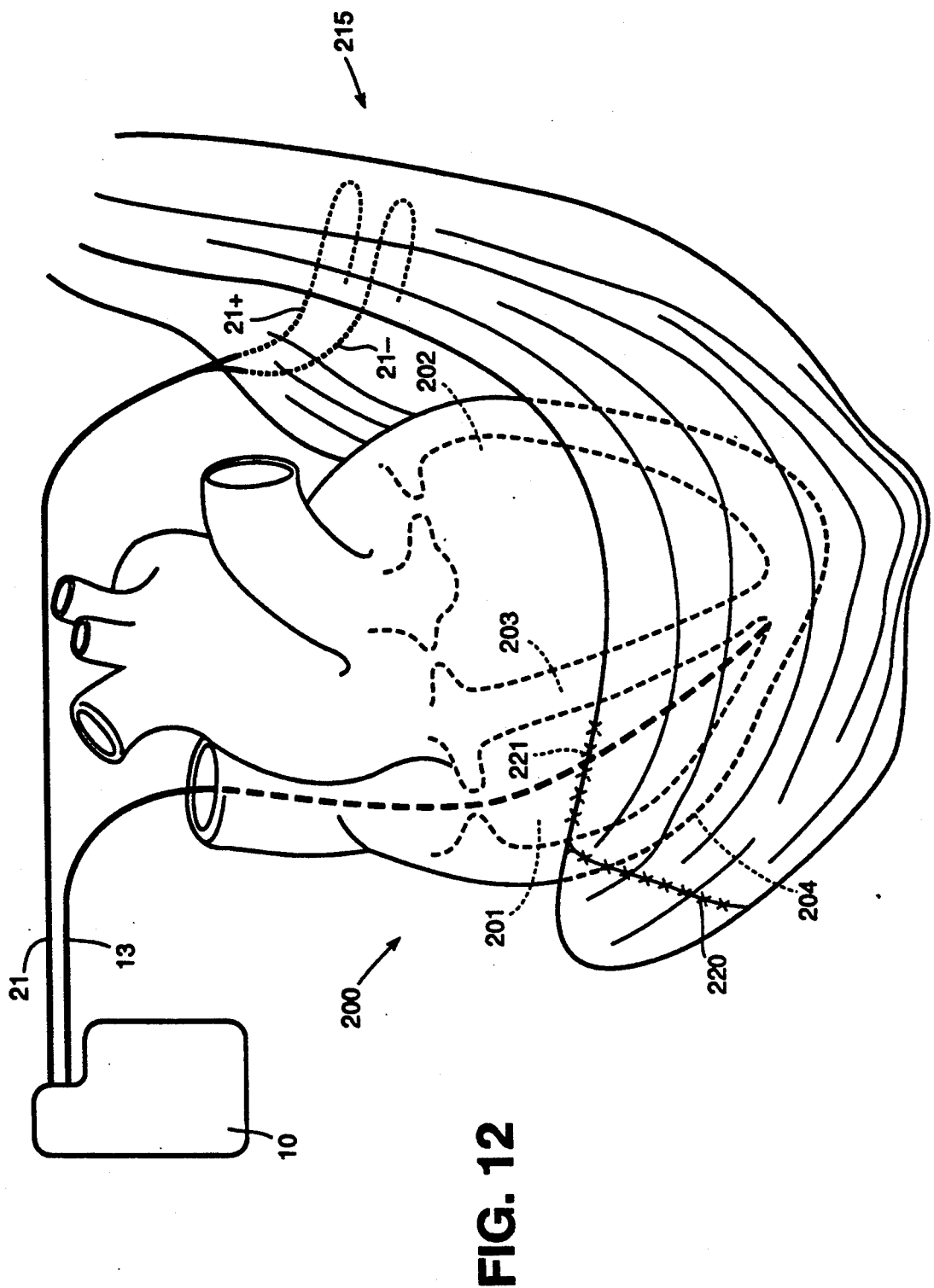
FIG. 12 illustrates one example of a bioelectrical stimulating device which performs cardiac assistance via long-term neuromuscular stimulation of skeletal muscle using systolic augmentation, and which employs an embodiment of the neuromuscular stimulating lead of the present invention.

FIG. 12 illustrates an example of a bioelectrical stimulating device 1 for performing both cardiac pacing and long-term stimulation of skeletal muscles for cardiac assistance using systolic augmentation, in accordance with one embodiment of the bioelectrical stimulating device of the present invention. A latissimus dorsi skeletal muscle graft 215 is positioned over the right ventricle 201 of a patient's heart 200. The longitudinal fibers of the latissimus dorsi graft 215 are oriented generally perpendicular to the longitudinal axes of the right ventricle 201, left ventricle 202 and interventricular septum 203 of the heart. The skeletal muscle is positioned in this manner so that when it is stimulated, it compresses the ventricles, particularly the left ventricle 202, and improves the force of right and left ventricular contraction. In a preferred configuration, the latissimus dorsi muscle graft 215 is wrapped around the heart 200 and fixedly attached to itself to form a cup-shaped "sling", using running sutures 220. Alternatively, the latissimus dorsi muscle graft 215 may be attached to the heart 200 along the borders of the right ventricular free wall 204 using running sutures 221.

A ventricular cardiac lead 13 is implanted in the heart's right ventricle 201 and the skeletal muscle lead 21 extends from the muscle stimulator 20 (of FIG. 9) to the latissimus dorsi muscle graft 215. The negative polarity (M−) skeletal muscle lead portion 21− is preferentially placed near nerve branches in the vicinity of the neuromuscular junction within the latissimus dorsi muscle graft 215 and the positive polarity (M+) skeletal muscle lead portion 21+ is implanted into the muscle a predetermined distance (i.e., 2 to 5 cm) from the negative polarity lead portion to provide for depolarization of intact motor nerve fibers. Placement of he electrodes in this manner lessens the possibility of nerve damage while increasing the selectivity of stimulation to particular muscle fibers. When an electrode of skeletal muscle lead 21 generates an electrical stimulation in the vicinity of a nerve fiber, it induces an electrical charge across the nerve membrane, causing an excess flow of ions through the membrane. At the site of a cathode electrode (M−), the potential outside the membrane becomes negative with respect to the inside potential. A weak cathodic potential cannot excite the fiber, but if this potential is increased above threshold, the nerve is excited. A further increase in stimulation amplitude above the threshold level does not augment the activity of the nerve.

In the heart, biological or artificial pacing stimulates electrical and mechanical activation, which proceeds in a continuous progression of excitation. In contrast, a contraction of skeletal muscle is modulated by the number of muscle fibers which are stimulated and the rate of stimulation. Rapid, repetitive stimuli which are delivered too frequently for individual muscle fibers to completely relax, result in a mechanical summation of contractile force until fusion occurs, causing the muscle to generate a considerable force.

A protocol for skeletal muscle electrostimulation commonly includes a progression from single stimulating impulses to a train of impulses at a predetermined rate e.g., 30 Hz). This progression takes place over a period of days or weeks. These impulses or bursts are coordinated with cardiac cycle timing.

Figure 13:
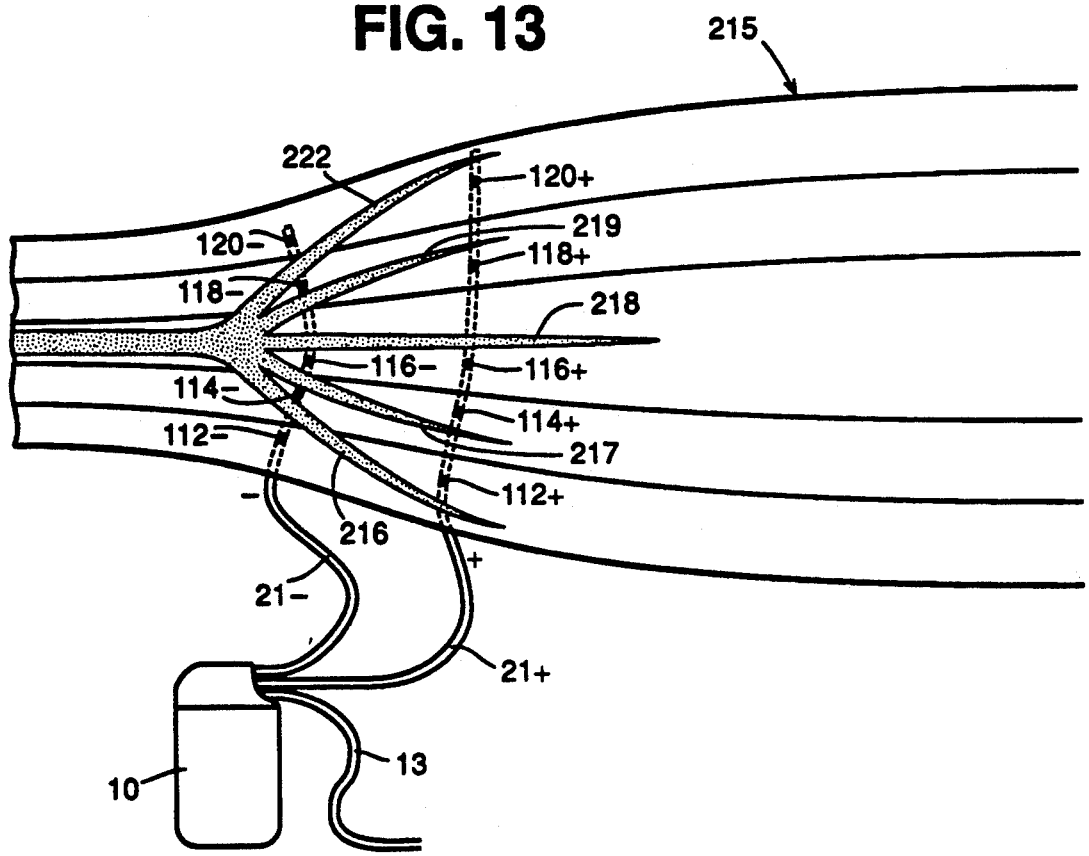
FIG. 13 depicts the interface between a multi-electrode neuromuscular stimulating lead of the present invention and a patient's latissimus dorsi muscle.

FIG. 13 is a depiction of the interface between a pair of FIG. 1 type multi-electrode neuromuscular stimulating leads 21, including a positive lead 21+ and a negative lead and 21−, and a patient's latissimus dorsi muscle 215. Different portions of the latissimus dorsi muscle 215 may be stimulated independently due to the capability for independent programming of stimulation timing, intensity and duration for the electrode pairs 112+ and 112−, 114+ and 114−, 116+ and 116−, 118+ and 118−, and 120+ and 120−. These electrode pairs are surgically placed in close proximity to nerve fiber branches 216, 217, 218, 219 and 222, respectively, so that each electrode pair will predominantly stimulate the appropriate nerve branch. The nerve fibers may have variable excitation thresholds due to differences in distance from an electrode pair to the nerve or variability in fiber diameter. Furthermore, variations in the muscle fibers which are innervated by a particular nerve fiber may produce differences in excitation threshold. Accordingly, the stimulation timing, intensity and pulse duration may be individually programmed following the surgical operation to produce an appropriate contraction behavior. The contractile performance of the muscle can be inspected visually during the implantation operation or inspected by means of ultrasonic imaging afterwards.

Figure 14:
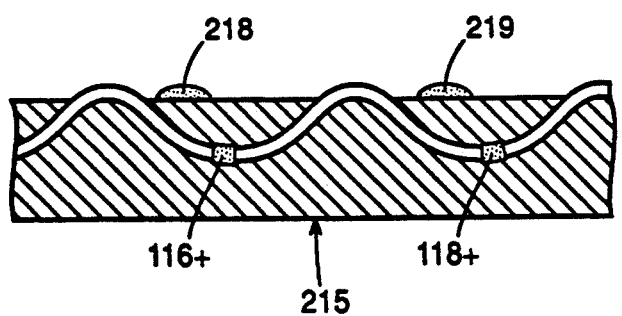
FIG. 14 illustrates a spatial configuration between electrodes of the multi-electrode stimulating lead of the present invention and nerve fibers in a latissimus dorsi muscle.

FIG. 14 illustrates a spatial configuration between electrodes 116+ and 118+ of the multi-electrode stimulating lead of the present invention, and nerve fibers 218 and 219 in a latissimus dorsi muscle 215. Here, the conductive portions of two intramuscular electrodes are placed in the muscle body and an electrical potential is applied between positive and negative electrode pairs to stimulate the muscle.

FIGS. 15 and 16 illustrate an example of an aortomyoplasty application of cardiac assistance. During systole, blood flows from the left ventricle to the aorta. At the end of systole, the aortic valve closes. To augment the flow of blood to the arteries, the latissimus dorsi muscle 215 is stimulated to contract and compress the aortic wall during diastole. As seen in FIG. 15, the latissimus dorsi muscle 215 is innervated by a number of nerve fiber branches, shown here as fiber branches 216, 217, 218, 219 and 222, which innervate different portions of the muscle. Accordingly, during surgical implantation, electrode pairs 112+ and 112−, 114+ and 114−, 116+ and 116−, 118+ and 118−, and 120+ and 120− are placed in the vicinity of the nerve fibers to stimulate muscle contraction in five segments. To ensure that blood will flow to the arteries, rather than backward to the heart, electrode pair 112+ and 112− are stimulated first, followed sequentially by pairs 114, 116, 118 and 120, with the synchronization delay gradually increasing for each subsequent pair as shown in FIG. 16. Furthermore, the amplitude, or intensity, of stimulation is generally strongest for electrode pair 112 and gradually is diminished for each successive electrode pair 114, 116, 118 and 120. Note that the stimulus intensity may be further varied due to differences in stimulation threshold for a given nerve fiber.

Figure 17:
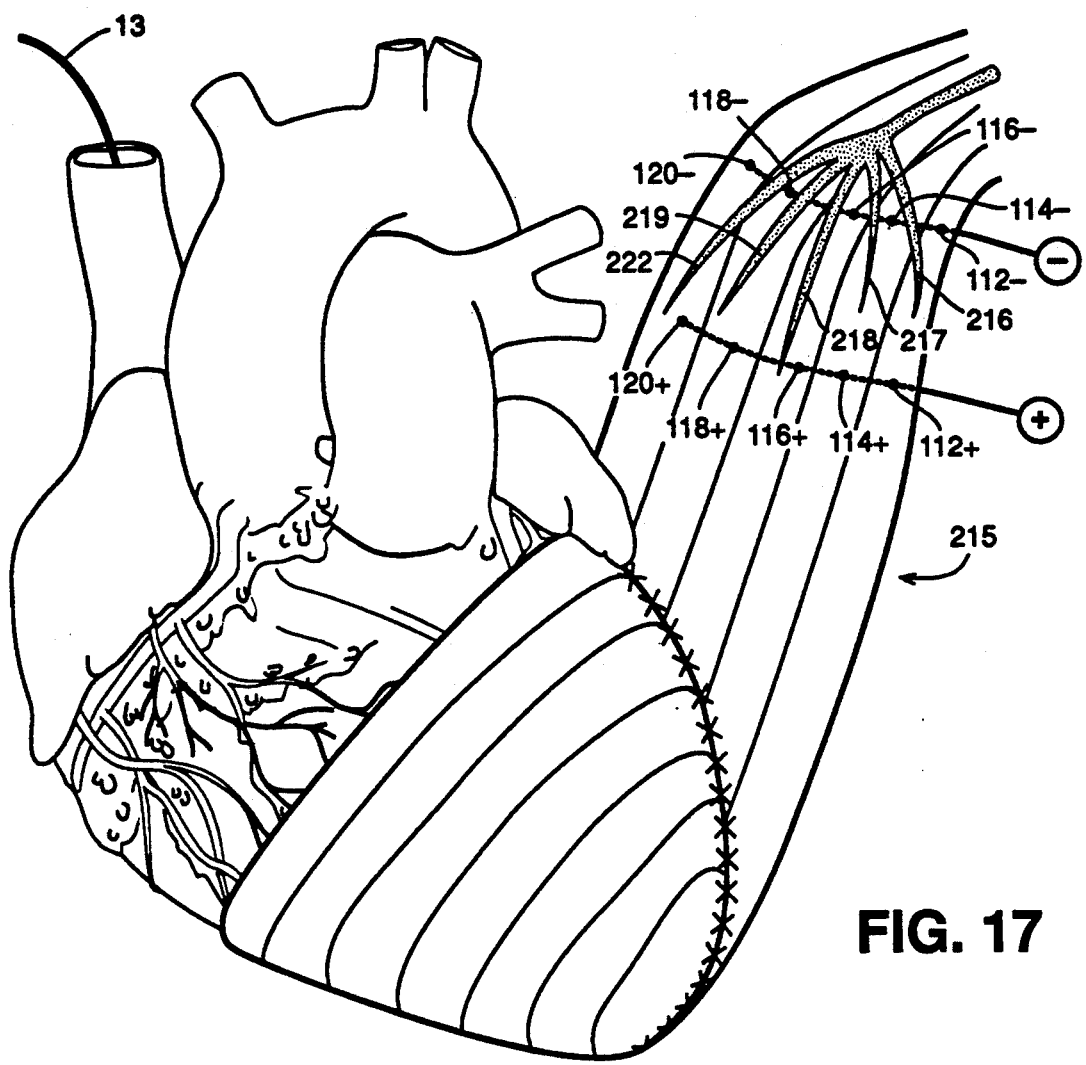
Figure 18:
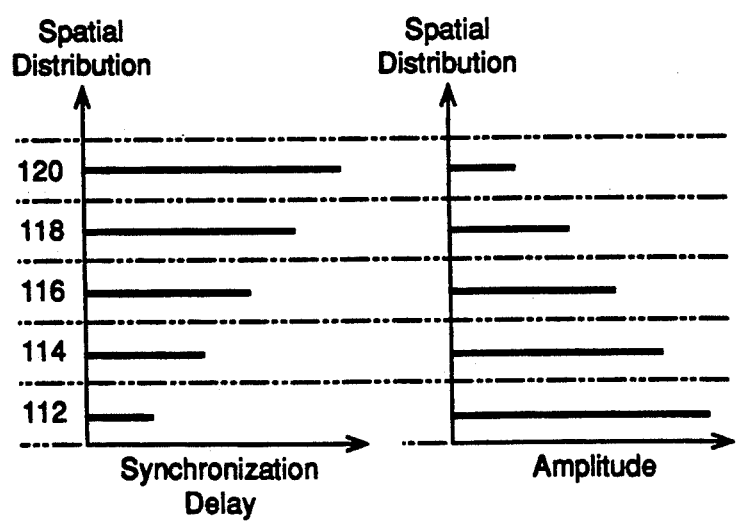
FIG. 18 is a graphical depiction of the manner of stimulating the skeletal muscle in a cardiomyoplasty application according to the teachings of the present invention.

In a similar manner, FIGS. 17 and 18 illustrate an example of a cardiomyoplasty application of cardiac assistance. During systole, blood flows from the left ventricle to the aorta. To enhance the flow of blood to the arteries, the latissimus dorsi muscle 215 is stimulated to contract and compress the ventricle during systole. As seen in FIG. 17, the latissimus dorsi muscle 215 is innervated by a number of nerve fiber branches, shown here as fiber branches 216, 217, 218, 219 and 222, which innervate different portions of the muscle. Accordingly, during surgical implantation, electrode pairs 112+ and 112−, 114+ and 114−, 116+ and 116−, 118+ and 118−, and 120+ and 120− are placed in the vicinity of the nerve fibers to stimulate muscle contraction in five segments. To assist the flow of blood into the aorta, electrode pair 112+ and 112− are stimulated first, followed sequentially by pairs 114, 116, 118 and 120 with the synchronization delay gradually increasing for each subsequent pair, as shown in FIG. 18. Furthermore, the amplitude, or intensity, of stimulation is generally strongest for electrode pair 112 and gradually is diminished for each successive electrode pair 214, 116, 118 and 120. Again, the stimulus intensity may be further varied due to differences in stimulation threshold for a given nerve fiber.

Figure 19:
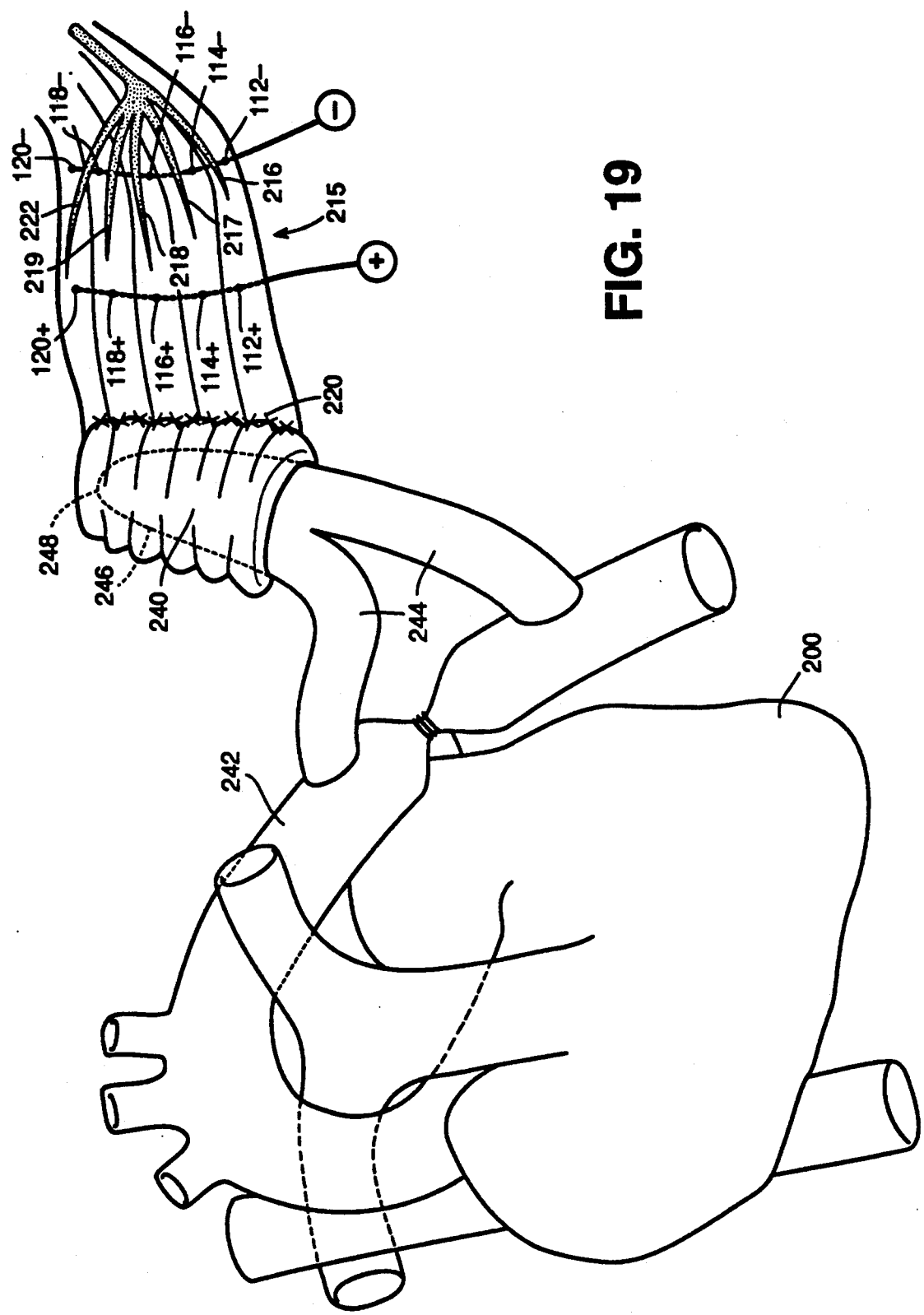
FIG. 19 illustrates one example of cardiac assistance being provided via long-term neuromuscular stimulation of skeletal muscle in a skeletal muscle ventricle.
Figure 20:
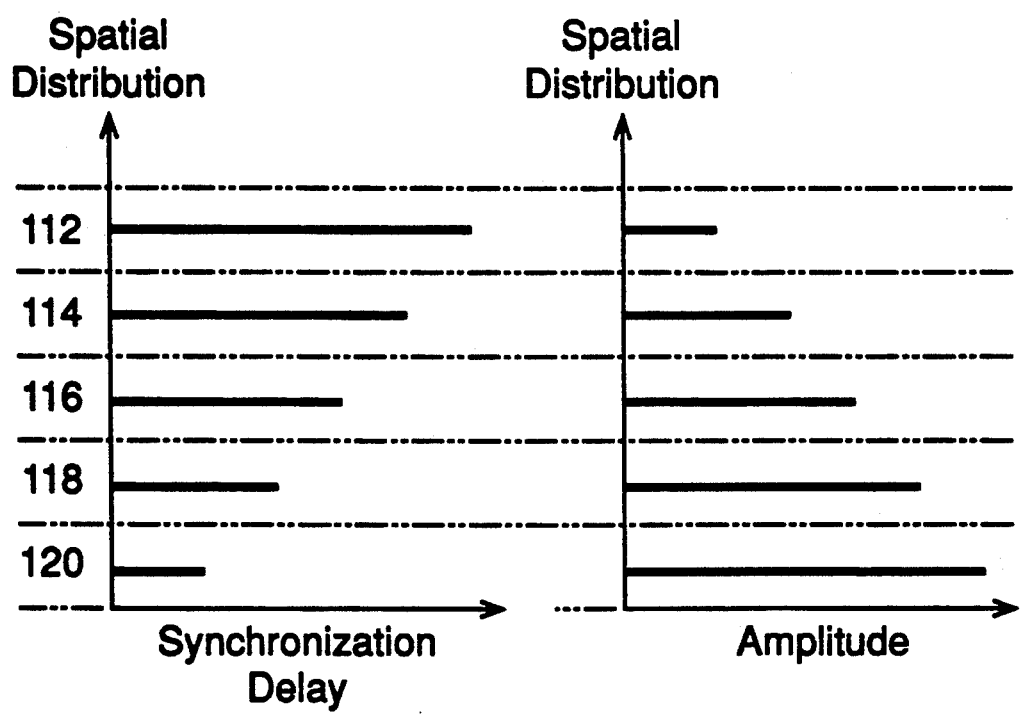
FIG. 20 is a graphical depiction of the manner of stimulating the skeletal muscle in a skeletal muscle ventricle application according to the teachings of the present invention.

FIGS. 19 and 20 show an example of a skeletal muscle ventricle application of cardiac assistance. A skeletal muscle ventricle operates in a manner similar to an aortomyoplasty application, but rather than wrapping skeletal muscle around the aorta, the muscle is wrapped around a cone-shaped mandrel 246 of material such as Teflon ®, made by E.I. Du Pont de Nemours and Company, 1007 Market Street, Wilmington, Del. 19898 (US). The mandrel 246 defines a cone-shaped cavity in the muscle wrap, which cavity is termed a "skeletal muscle ventricle" (SMV) 240. The mandrel 246 is surgically placed in the body for a predetermined time (for example, four weeks), after which time it is removed and the skeletal muscle may be stimulated to contract about the SMV. The skeletal muscle ventricle 240 is surgically interconnected to the descending aorta 242 using a synthetic bifurcation graft 244. The bifurcation graft 244 may be constructed from a material such as Gore-Tex ®, made by W. L. Gore & Associates, Inc., 551 Paper Mill Road, P.O. Box 9329, Newark, Del. 19714 (US). During systole, blood flows from the left ventricle to the descending aorta 242. At the end of systole, the aortic valve closes. To augment the flow of blood to the arteries, the latissimus dorsi muscle 215 is stimulated to contract and compress the skeletal muscle ventricle 240 during diastole.

As seen in FIG. 19, the latissimus dorsi muscle 215 is innervated by a number of nerve fibers, shown here as fibers 216, 217, 218, 219 and 222, which innervate different portions of the muscle. Accordingly, during surgical implantation, electrode pairs 112+ and 112−, 114+ and 114−, 116+ and 116−, 118+ and 118−, and 120+ and 120− are placed in the vicinity of the respective nerve fibers 216-219 and 222 to stimulate muscle contraction in five segments. To assist blood flow to the arteries the skeletal muscle at the apex or tip 248 of the cone of skeletal muscle ventricle 240 is stimulated first, followed sequentially by muscle segments positioned between the apex 248 and the base of the cone. Therefore, electrode pair 120+ and 120− is stimulated first, followed sequentially by pairs 118, 116, 114 and 112, with the synchronization delay gradually increasing for each subsequent pair, as shown in FIG. 20. Furthermore, the intensity of stimulation is generally strongest for electrode pair 120 and gradually is diminished for each successive electrode pair. As is the case with other cardiac assistance stimulation, the stimulus intensity may be variable due to differences in stimulation threshold for a given nerve fiber.

From the foregoing discussion, it is apparent that the present invention provides a neuromuscular stimulating lead and device for generating stimulating pulses on the lead, which accomplishes substantial improvement in the hemodynamics of a patient's cardiovascular system and results in an augmented cardiac output and stroke volume. Multiple stimulation channels and multiple electrode leads, which may be independently programmed in terms of stimulation intensity, timing and duration, produce this improvement by providing the capability of sequentially contracting a surgically implanted cardiac assistance skeletal muscle to pump blood in a desired direction.

Although the invention has been shown and described with reference to a particular embodiment, it is to be understood that these embodiments are merely illustrative of the application of the principles of the invention. Numerous modifications may be made therein and other arrangements may be devised without departing from the true spirit and scope of the invention.

What is claimed is:

1. An implantable neuromuscular stimulating apparatus, comprising:
   a plurality of channels for stimulating a patient's skeletal muscle that has been surgically prepared to perform cardiac assistance;
   neuromuscular stimulating pulse generator means for generating electrical pulses in said plurality of channels to stimulate the skeletal muscle in coordination with the patient's cardiac cycle, said generator means being constructed and arranged to control at least one characteristic parameter of the electrical pulses, the characteristic parameter being selected from the group, consisting of intensity, pulse duration, number of pulses per burst, interpulse interval within a burst, pulse timing and burst timing;
   a first electrode for each of said plurality of channels and at least one ground electrode, said first electrodes and said at least one ground electrode being coupled to said generator means and being adapted to be coupled to excitable tissue in the patient's skeletal muscle for applying pulses generated by said neuromuscular stimulating pulse generator means between said first and ground electrodes;
   means for fixing said first electrodes for each of said plurality of channels and said at least one ground electrode in close proximity to preselected nerve fibers within the patient's skeletal muscle; and
   means for controlling said pulse generator means to govern the at least one characteristic parameter of the electrical pulses in said plurality of channels to sequentially excite each of a first channel and a plurality of subsequent channels of said plurality of channels in a predetermined order, causing the patient's skeletal muscle to sequentially contract in a coordinated manner from one portion thereof to another.

2. An apparatus in accordance with claim 1, wherein said pulse generator controlling means further comprises means for timing and sequentially exciting each subsequent channel of said plurality of channels with an increasing delay with respect to the patient's cardiac cycle.

3. An apparatus in accordance with claim 2, wherein said pulse generator controlling means further comprises means for sequentially exciting each subsequent channel of said plurality of channels with a decreasing intensity.

4. An apparatus in accordance with claim 1, wherein said patient's skeletal muscle surgical preparation is a cardiomyoplasty preparation and the patient's latissimus dorsi muscle is wrapped around the heart, and wherein said pulse generator controlling means further comprises:
   means for determining when the patient's heart is in systole;
   means for initiating stimulation in response to a determination by said determining means that the patient's heart is in systole; and
   means for sequentially exciting each subsequent channel of said plurality of channels with an increasing delay with respect to the patient's cardiac cycle such that the skeletal muscle at the apex of the patient's heart contracts first and the contraction proceeds sequentially in an anterior direction.

5. An apparatus in accordance with claim 4, wherein said pulse generator controlling means further comprises means for sequentially exciting each subsequent channel of said plurality of channels with a decreasing intensity.

6. An apparatus in accordance with claim 1, wherein said first electrode comprises a first implantable multi-electrode intramuscular lead for each of said plurality of channels and wherein said at least one ground electrode comprises a second implantable multi-electrode intramuscular lead.

7. An apparatus in accordance with claim 6, wherein said first and second implantable multi-electrode intramuscular leads each further comprise:
   a plurality of electrical conductors, each of said electrical conductors extending from a proximal end portion thereof to a tapered distal end portion thereof corresponding to proximal and distal end portions, respectively, of the lead, insulating material enclosing each of said conductors and electrically separating said conductors from one another, electrical connector means for electrically coupling the channels of said neuromuscular stimulating pulse generator means to the proximal end portions of corresponding ones of said electrical conductors, and corresponding neuromuscular stimulating electrodes electrically coupled to the distal end portions of said electrical conductors, each of said stimulating electrodes having an uninsulated surface in said tapered distal end portion for directly contacting the patient's muscle tissue in close proximity to muscle activating nerve branches at said uninsulated surface; and
   a section of suture material having a proximal end fixedly attached to a distal end of the tapered distal end portion of the lead for firmly affixing at least a portion of said tapered distal end portion of the lead into the patient's tissue adjacent said nerve branches.

8. An implantable neuromuscular stimulating apparatus, comprising:
   a plurality of channels for stimulating a patient's skeletal muscle that has been surgically prepared to perform cardiac assistance;
   neuromuscular stimulating pulse generator means for generating electrical pulses in said plurality of channels to stimulate the skeletal muscle in coordination with the patient's cardiac cycle, said generator means being constructed and arranged to control at least one characteristic parameter of the electrical pulses, the characteristic parameter being selected from a group consisting of intensity, pulse duration, number of pulses per burst, interpulse interval within a burst, pulse timing and burst timing;
   a first electrode for each of said plurality of channels and at least one ground electrode, said first electrodes and said at least one ground electrode being coupled to said generator means and being adapted to be coupled to excitable tissue in the patient's skeletal muscle for applying pulses generated by said neuromuscular stimulating pulse generator means between said first and ground electrodes;
   means for affixing said first electrodes for each of said plurality of channels and said at least one ground electrode in close proximity to preselected nerve fibers within the patient's skeletal muscle; and
   means for controlling said pulse generator means to govern the at least one characteristic parameter of the electrical pulses in said plurality of channels to sequentially excite each of a first channel and at least one subsequent channel of said plurality of channels in a predetermined order, causing the patient's skeletal muscle to sequentially contract in a coordinated manner from one portion thereof to another;

said patient's skeletal muscle surgical preparation being an aortomyoplasty preparation and the patient's latissimus dorsi muscle being wrapped around the aorta, and said pulse generator controlling means further comprising:

means for determining when the patient's heart is in diastole;

means for initiating stimulation in response to a determination by said determining means that the patient's heart is in diastole; and means for sequentially exciting each subsequent channel of said plurality of channels with an increasing delay with respect to the patient's cardiac cycle such that the skeletal muscle located in a proximal portion of the aorta contracts first and the contraction proceeds sequentially in a distal direction.

9. An apparatus in accordance with claim 8, wherein said pulse generator controlling means further comprises means for sequentially exciting each subsequent channel of said plurality of channels with a decreasing intensity.

10. An implantable neuromuscular stimulating apparatus, comprising:

a plurality of channels for stimulating a patient's skeletal muscle that has been surgically prepared to perform cardiac assistance;

neuromuscular stimulating pulse generator means for generating electrical pulses in said plurality of channels to stimulate the skeletal muscle in coordination with the patient's cardiac cycle, said generator means being constructed and arranged to control at least one characteristic parameter of the electrical pulses, the characteristic parameter being selected from a group consisting of intensity, pulse duration, number of pulses per burst, interpulse interval within a burst, pulse timing and burst timing;

a first electrode for each of said plurality of channels and at least one ground electrode, said first electrodes and said at least one ground electrode being coupled to said generator means and being adapted to be coupled to excitable tissue in the patient's skeletal muscle for applying pulses generated by said neuromuscular stimulating pulse generator means between said first and ground electrodes;

means for affixing said first electrodes for each of said plurality of channels and said at least one ground electrode in close proximity to preselected nerve fibers within the patient's skeletal muscle; and means for controlling said pulse generator means to govern the at least one characteristic parameter of the electrical pulses in said plurality of channels to sequentially excite each of a first channel and at least one subsequent channel of said plurality of channels in a predetermined order, causing the patient's skeletal muscle to sequentially contract in a coordinated manner from one portion thereof to another;

said patient's skeletal muscle surgical preparation being a skeletal muscle ventricle preparation and the patient's latissimus dorsi muscle being wrapped around a small diameter reservoir having a generally conic shape with an apex and a base portion, and said pulse generator controlling means further comprising:

means for determining when the patient's heart is in diastole;

means for initiating stimulation in response to a determination by said determining means that the patient's heart is in diastole; and means for sequentially exciting each subsequent channel of said plurality of channels with an increasing delay with respect to the patient's cardiac cycle such that the skeletal muscle located at the apex of the reservoir contracts first and the contraction proceeds sequentially toward the base portion of the reservoir.

11. An apparatus in accordance with claim 10, wherein said pulse generator controlling means further comprises means for sequentially exciting each subsequent channel of said plurality of channels with a decreasing intensity.

12. A method of stimulating a patient's skeletal muscle using an implantable neuromuscular stimulating apparatus having a plurality of channels, said muscle having been surgically prepared to perform cardiac assistance, comprising the steps of:

affixing a first electrode for each of said plurality of channels in close proximity to preselected nerve fibers within the patient's skeletal muscle;

affixing at least one ground electrode within the patient's body;

generating electrical pulses between said first electrodes and said at least one ground electrode in said plurality of channels to stimulate the skeletal muscle in coordination with the patient's cardiac cycle, said electrical pulses having variable intensity, duration and timing; and controlling said pulse generation step to govern the variable intensity, duration and timing of the electrical pulses in said plurality of channels to sequentially excite each of a first channel and a plurality of subsequent channels in said plurality of channels in a predetermined order, causing the patient's skeletal muscle to sequentially contract in a coordinated manner from one portion thereof to another.

13. A method in accordance with claim 12, wherein said controlling step comprises the substeps of:

timing a delay interval with respect to the patient's cardiac cycle for each of said plurality of channels;

increasing the timed delay interval for each subsequent channel of said plurality of channels; and exciting each channel according to the increased timed delay interval with a predetermined excitation intensity.

14. A method in accordance with claim 13, wherein said controlling step further comprises the substeps of:

decreasing the excitation intensity for each subsequent channel of said plurality of channels; and exciting each channel according to the decreased intensity.

15. A method in accordance with claim 12, wherein said patient's skeletal muscle surgical preparation is a cardiomyoplasty preparation and the patient's latissimus dorsi muscle is wrapped around the heart, and wherein said pulse generator controlling step further comprises the steps of:

determining when the patient's heart is in systole;

initiating stimulation in response to said determination that the patient's heart is in systole;

sequentially exciting each subsequent channel of said plurality of channels with an increasing delay with respect to the patient's cardiac cycle such that the skeletal muscle at the apex of the patient's heart contracts first and the contraction proceeds sequentially in an anterior direction.

16. A method in accordance with claim 15, wherein said pulse generation controlling step further comprises the substep of sequentially exciting each subsequent channel of said plurality of channels with a decreasing intensity.

17. A method of stimulating a patient's skeletal muscle using an implantable neuromuscular stimulating apparatus having a plurality of channels, said muscle having been surgically prepared to perform cardiac assistance, comprising the steps of:

affixing a first electrode for each of said plurality of channels in close proximity to preselected nerve fibers within the patient's skeletal muscle;

affixing at least one ground electrode within the patient's body;

generating electrically pulses between said first electrodes and said at least one ground electrode in said plurality of channels to stimulate the skeletal muscle in coordination with the patient's cardiac cycle, said electrical pulses having variable intensity, duration and timing; and controlling said pulse generation step to govern the variable intensity, duration and timing of the electrical pulses in said plurality of channels to sequentially excite each of a first channel and at least one subsequent channel of said plurality of channels in a predetermined order, causing the patient's skeletal muscle to sequentially contract in a coordinated manner from one portion thereof to another;

said patient's skeletal muscle surgical preparation being a skeletal muscle ventrical preparation and the patient's latissimus dorsi muscle being wrapped around a small diameter reservoir having a generally conic shape with an apex and a base portion, and said pulse generation controlling step further comprising the substeps of:

determining when the patient's heart is in diastole;

initiating stimulation in response to a determination by said determining means that the patient's heart is in diastole;

sequentially exciting each subsequent channel of said plurality of channels with an increasing delay with respect to the patient's cardiac cycle such that the skeletal muscle located at the apex of the reservoir contracts first and the contraction proceeds sequentially toward the base portion of the reservoir.

18. A method in accordance with claim 17, wherein said pulse generation controlling step further comprises the substep of sequentially exciting each subsequent channel of said plurality of channels with a decreasing intensity.

19. A method of stimulating a patient's skeletal muscle using an implantable neuromuscular stimulating apparatus having a plurality of channels, said muscle having been surgically prepared to perform cardiac assistance, comprising the steps of:

affixing a first electrode for each of said plurality of channels in close proximity to preselected nerve fibers within the patient's skeletal muscle;

affixing at least one ground electrode within the patient's body;

generating electrical pulses between said first electrodes and said at least one ground electrode in said plurality of channels to stimulate the skeletal muscle in coordination with the patient's cardiac cycle, said electrical pulses having variable intensity, duration and timing; and controlling said pulse generation step to govern the variable intensity, duration and timing of the electrical pulses in said plurality of channels to sequentially excite each of a first channel and at least one subsequent channel of said plurality of channels in a predetermined order, causing the patient's skeletal muscle to sequentially contract in a coordinated manner from one portion thereof to another;

said patient's skeletal muscle surgical preparation being an aortomyoplasty preparation and the patient's latissimus dorsi muscle being wrapped around the aorta, and said pulse generator controlling step further comprising the substeps of:

determining when the patient's heart is in diastole;

initiating stimulation in response to said determination that the patient's heart is in diastole;

sequentially exciting each subsequent channel of said plurality of channels with an increasing delay with respect to the patient's cardiac cycle such that the skeletal muscle located in a proximal portion of the aorta contracts first and the contraction proceeds sequentially in a distal direction.

20. A method in accordance with claim 19, wherein said pulse generation controlling step further comprises the substep of sequentially exciting each subsequent channel of said plurality of channels with a decreasing intensity.

* * * * *